(12) United States Patent
O'Hern et al.

(10) Patent No.: US 8,597,173 B2
(45) Date of Patent: Dec. 3, 2013

(54) PELVIC FLOOR TREATMENTS AND RELATED TOOLS AND IMPLANTS

(75) Inventors: Jeffrey Michael O'Hern, Minnetonka, MN (US); Richard Kaleta, Minnetonka, MN (US); Chaouki A. Khamis, Minnetonka, MN (US); Gary A. Rocheleau, Minnetonka, MN (US); John F. Otte, Minnetonka, MN (US); Gregory L. Koeller, Minnetonka, MN (US); David J. Kupiecki, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 718 days.

(21) Appl. No.: 12/669,099

(22) PCT Filed: Jul. 25, 2008

(86) PCT No.: PCT/US2008/009066
§ 371 (c)(1),
(2), (4) Date: May 13, 2010

(87) PCT Pub. No.: WO2009/017680
PCT Pub. Date: Feb. 5, 2009

(65) Prior Publication Data
US 2010/0261955 A1 Oct. 14, 2010

Related U.S. Application Data

(60) Provisional application No. 60/952,411, filed on Jul. 27, 2007, provisional application No. 61/012,260, filed on Dec. 7, 2007.

(51) Int. Cl.
*A61F 2/00* (2006.01)

(52) U.S. Cl.
USPC .............................................. 600/37; 600/29

(58) Field of Classification Search
USPC .......... 600/29, 30, 37; 606/151; 128/897–899
See application file for complete search history.

(56) References Cited

U.S. PATENT DOCUMENTS 4,172,458 A  10/1979  Pereyra
4,741,330 A   5/1988  Hayhurst
(Continued)

FOREIGN PATENT DOCUMENTS

EP  0248544 A1  12/1987
EP  0571686     12/1993
(Continued)

OTHER PUBLICATIONS

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

(Continued)

*Primary Examiner* — Charles A Marmor, II
*Assistant Examiner* — Shannon McBride
(74) *Attorney, Agent, or Firm* — Kagan Binder, PLLC

(57) ABSTRACT

Described are implants, tools, and methods useful for treating pelvic conditions such as prolapse, by placing an implant to support pelvic tissue, the implants, tools, and methods involving one or more of adjusting engagements, specific implants and pieces of implants, placement of implants at locations within the pelvic region, and insertion, adjusting, and grommet management tools.

18 Claims, 16 Drawing Sheets

(56) References Cited

U.S. PATENT DOCUMENTS

| | | |
|---|---|---|
| 5,163,960 A | 11/1992 | Bonutti |
| 5,167,665 A | 12/1992 | McKinney |
| 5,326,205 A | 7/1994 | Anspach et al. |
| 5,368,602 A | 11/1994 | De La Torre |
| 5,464,424 A | 11/1995 | O'Donnell, Jr. |
| 5,591,206 A | 1/1997 | Moufarrege |
| 5,647,836 A | 7/1997 | Blake, III et al. |
| 5,922,026 A | 7/1999 | Chin |
| 6,221,060 B1 * | 4/2001 | Willard .................. 604/264 |
| 6,248,118 B1 | 6/2001 | Tanner et al. |
| 6,306,079 B1 | 10/2001 | Trabucco |
| 6,443,988 B2 | 9/2002 | Felt et al. |
| 6,502,578 B2 | 1/2003 | Raz et al. |
| 6,514,194 B2 | 2/2003 | Schweich et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,612,977 B2 * | 9/2003 | Staskin et al. .................. 600/30 |
| 6,641,524 B2 | 11/2003 | Kovac |
| 6,648,921 B2 | 11/2003 | Anderson |
| 6,669,735 B1 | 12/2003 | Pelissier |
| 6,808,486 B1 * | 10/2004 | O'Donnell .................. 600/30 |
| 6,884,212 B2 | 4/2005 | Thierfelder et al. |
| 7,070,558 B2 | 7/2006 | Gellman et al. |
| 7,087,065 B2 | 8/2006 | Ulmsten et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,189,251 B2 | 3/2007 | Kay |
| 7,347,812 B2 | 3/2008 | Mellier |
| 7,351,197 B2 | 4/2008 | Montpetit et al. |
| 7,393,320 B2 | 7/2008 | Montpetit et al. |
| 7,407,480 B2 | 8/2008 | Staskin |
| 7,422,557 B2 | 9/2008 | Arnal et al. |
| 7,494,495 B2 | 2/2009 | Delorme et al. |
| 7,500,945 B2 | 3/2009 | Cox |
| 7,517,313 B2 | 4/2009 | Thierfelder et al. |
| 7,588,598 B2 | 9/2009 | Delorme et al. |
| 7,608,036 B2 | 10/2009 | Raz et al. |
| 7,740,576 B2 | 6/2010 | Hodroff |
| 7,794,385 B2 | 9/2010 | Rosenblatt |
| 7,914,437 B2 | 3/2011 | Gozzi et al. |
| 2002/0028980 A1 | 3/2002 | Thierfelder et al. |
| 2002/0147382 A1 | 10/2002 | Neisz et al. |
| 2003/0023137 A1 | 1/2003 | Gellman et al. |
| 2003/0130670 A1 | 7/2003 | Anderson et al. |
| 2003/0171644 A1 | 9/2003 | Anderson et al. |
| 2003/0176875 A1 | 9/2003 | Anderson |
| 2003/0181924 A1 | 9/2003 | Yamamoto et al. |
| 2003/0212305 A1 | 11/2003 | Anderson et al. |
| 2003/0225424 A1 | 12/2003 | Benderev |
| 2004/0015057 A1 | 1/2004 | Rocheleau et al. |
| 2004/0039453 A1 | 2/2004 | Anderson et al. |
| 2004/0220591 A1 | 11/2004 | Bonutti |
| 2004/0225181 A1 | 11/2004 | Chu et al. |
| 2004/0267088 A1 | 12/2004 | Kammerer |
| 2005/0004426 A1 | 1/2005 | Raz et al. |
| 2005/0004427 A1 | 1/2005 | Cervigni |
| 2005/0148815 A1 | 7/2005 | Mortier et al. |
| 2005/0199249 A1 | 9/2005 | Karram |
| 2005/0245787 A1 | 11/2005 | Cox et al. |
| 2005/0250977 A1 * | 11/2005 | Montpetit et al. .................. 600/29 |
| 2005/0278037 A1 | 12/2005 | Delorme et al. |
| 2005/0283189 A1 | 12/2005 | Rosenblatt |
| 2006/0122457 A1 | 6/2006 | Kovac |
| 2006/0173237 A1 | 8/2006 | Jacquetin |
| 2006/0195007 A1 | 8/2006 | Anderson et al. |
| 2006/0195010 A1 | 8/2006 | Arnal et al. |
| 2006/0195011 A1 | 8/2006 | Arnal |
| 2006/0224038 A1 | 10/2006 | Rao |
| 2007/0062541 A1 | 3/2007 | Zhou et al. |
| 2007/0173864 A1 | 7/2007 | Chu |
| 2008/0021265 A1 | 1/2008 | Garbin et al. |
| 2008/0027271 A1 | 1/2008 | Maccarone |
| 2008/0039678 A1 | 2/2008 | Montpetit et al. |
| 2008/0045782 A1 | 2/2008 | Jimenez |
| 2008/0132754 A1 | 6/2008 | Thierfelder et al. |
| 2009/0005634 A1 | 1/2009 | Rane |
| 2009/0012353 A1 | 1/2009 | Beyer |
| 2009/0137864 A1 | 5/2009 | Cox et al. |
| 2009/0240102 A1 | 9/2009 | Rane et al. |
| 2010/0105979 A1 | 4/2010 | Hamel et al. |
| 2010/0152528 A1 | 6/2010 | Chapman et al. |
| 2010/0174134 A1 | 7/2010 | Anderson et al. |
| 2010/0261952 A1 | 10/2010 | Montpetit et al. |
| 2010/0298630 A1 | 11/2010 | Wignall |

FOREIGN PATENT DOCUMENTS

| | | |
|---|---|---|
| EP | 1060714 A3 | 9/2002 |
| FR | 2852817 | 10/2004 |
| IT | 1299162 | 4/1998 |
| WO | WO9835616 A1 | 8/1998 |
| WO | WO9835632 A1 | 8/1998 |
| WO | WO9840114 | 9/1998 |
| WO | WO9916381 A1 | 4/1999 |
| WO | WO0064370 A1 | 2/2000 |
| WO | WO0027304 A1 | 5/2000 |
| WO | WO0057812 A1 | 10/2000 |
| WO | WO0074633 A2 | 12/2000 |
| WO | WO0106951 A1 | 2/2001 |
| WO | WO02078552 A1 | 10/2002 |
| WO | WO03003778 A2 | 4/2003 |
| WO | WO03028585 A2 | 4/2003 |
| WO | WO03047476 A1 | 6/2003 |
| WO | WO03068107 A1 | 8/2003 |
| WO | WO03073960 A1 | 9/2003 |
| WO | WO03077772 A1 | 9/2003 |
| WO | WO03096929 A1 | 11/2003 |
| WO | WO2004012626 A1 | 2/2004 |
| WO | WO2004017845 A1 | 3/2004 |
| WO | WO2004045457 A1 | 6/2004 |
| WO | WO2005037132 A2 | 4/2005 |
| WO | WO2005087153 A2 | 9/2005 |
| WO | WO2005094741 A1 | 10/2005 |
| WO | WO2005110274 A1 | 11/2005 |
| WO | WO2005112842 A1 | 12/2005 |
| WO | WO2006069078 A2 | 6/2006 |
| WO | WO2006108145 A1 | 10/2006 |
| WO | WO2007002071 A1 | 1/2007 |
| WO | WO2007014241 A1 | 2/2007 |
| WO | WO2007016083 A1 | 2/2007 |
| WO | WO2007016698 A1 | 2/2007 |
| WO | WO2007059368 A1 | 5/2007 |
| WO | WP2007059199 A2 | 5/2007 |
| WO | WO2007081954 A1 | 7/2007 |
| WO | WO2007081955 A1 | 7/2007 |
| WO | WO2007097994 A2 | 8/2007 |
| WO | WO2007146784 A2 | 12/2007 |
| WO | WO2007149348 A2 | 12/2007 |
| WO | WO2007149555 A2 | 12/2007 |
| WO | WO2008013867 A1 | 1/2008 |
| WO | WO2008015722 A1 | 2/2008 |
| WO | WO2008042438 A2 | 4/2008 |
| WO | WO2008057269 A1 | 5/2008 |
| WO | WO2008083394 A2 | 7/2008 |
| WO | WO2008085825 A1 | 7/2008 |
| WO | WO2008124056 A1 | 10/2008 |
| WO | WO2009005714 A2 | 1/2009 |
| WO | WO2009011852 A1 | 1/2009 |
| WO | WO2009038781 A1 | 3/2009 |
| WO | WO2009075800 A1 | 6/2009 |
| WO | WO2009145911 A1 | 12/2009 |
| WO | WO2010129331 A2 | 11/2010 |

OTHER PUBLICATIONS

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Cervigni, Mauro et al., The Use of Synthetics in the Treatment of Pelvic Organ Prolapse, Voiding Dysfunction and Female Urology, vol. 11, pp. 429-435 (2001).

(56) References Cited

OTHER PUBLICATIONS

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, G ynecologie Obstetrieue & Fertilite, vol. 31, Issue 1, pp. 14-19 (Jan. 2003).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce With Marlex Mesh for Treatment of Cystoceles, International Urogynecology Journal, vol. 9, pp. 200-204 (1998).

Guner, et al., Transvaginal Sacrospinous Colpopexy for Marked Uterovaginal Vault Prolapse, Inter J of Gynec & Obstetrics, vol. 74, pp. 165-170 (2001).

IVS Tunneller, Australian Medical Design Breakthrough for GSI, mixed incontinence and vault prolapse, AMA Medical Products, 4 pages (no date).

Julian, Thomas, The Efficacy of Marlex Mesh in the Repair of Sever, Recurrent vaginal Prolapse of the Anterior Midvaginal Wall, Am J Obstet Gynecol, vol. 175, n. 6, pp. 1472-1475 (Dec. 1996).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Lichtenstein, Irving L. et al, The Tension Free Hernioplasty, The American Journal of Sugery, vol. 157 pp. 188-193 (Feb. 1989).

Marchionni, Mauro et al., True Incidence of Vaginal Vault Prolapse—Thirteen Years Experience, Journal of Reproductive Medicine, vol. 44, n. 8, pp. 679-684 (Aug. 199)

Marinkovic, Serge Peter et al., Triple Compartment Prolapse: Sacrocolpopexy with Anterior and Posterior Mesh Extensions, Br J Obstet Gynaecol, vol. 110, pp. 323-326 (Mar. 2003).

Migliari, Roberto et al., Tension-Free Vaginal Mesh Repair for Anterior Vaginal Wall Prolapse. Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morley, George W. et al., Sacrospinous Ligament Fixations for Eversion of the Vagina, Am. J Obstet Gyn, vol. 158, n. 4, pp. 872-881 (Apr. 1988).

Nicita, Giulio, A New Operation for Genitourinary Prolapse, Journal of Urology. vol. 160, pp. 741-745 (Sep. 1998).

Paraiso et al., Laparoscopic Surgery for Enterocele, Vaginal Apex Prolapse and Rectocele, Int. Urogynecol J, vol. 10, pp. 223-229 (1999).

Petros, Peter E. Papa et al., Pelvic Floor Rehabilitation According to the Integrated Theory of Female Urinary Incontinence, Chapter 7, pp. 249-258 (book chapter).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pa.

Petros, Peter E. Papa, Vault Prolapse II; Restoration of dynamic Vaginal Supports by Infracoccygeal Sacropexy, An Axial Day-Case Vaginal Procedure, Int Urogynecol J, vol. 12, pp. 296-303 (2001).

Richter, K., Massive Eversion of the Vagina: Pathogenesis, Diagnosis and Therapy of the "True" Prolapse of the Vaginal Stump, Clin obstet gynecol, vol. 25, pp. 897-912 (1982).

Sullivan, Eugene S. et al., Total Pelvic Mesh Repair a Ten-Year Experience, Dis. Colon Rectum, vol. 44, No. 6, pp. 857-863 (Jun. 2001).

Swift, S.E., et al., Case-Control Study of Etiologic Factors in the Development of Sever Pelvic Organ Prolapse, Int Urogynecol J, vol. 12, pp. 187-192 (2001).

Visco, Anthony G. et al., Vaginal Mesh Erosion After Abdominal Sacral Colpopexy, Am J Obstet Gynecol, vol. 184, n. 3, pp. 297-302 (297-302).

Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).

Winters et al., Abdominal Sacral Colpopexy and Abdominal Enterocele Repair in the Management of Vaginal Vault Prolapse, Urology, vol. 56, supp. 6A, pp. 55-63 (2000).

Zacharin, Robert et al., Pulsion Enterocele: Long-Term Results of an Abdominoperineal Technique, Obstetrics & Gynecology, vol. 55 No. 2, pp. 141-148 (Feb. 1980).

Mouly, Patrick et al., Vaginal Reconstruction of a Complete Vaginal Prolapse: The Trans Obturator Repair, Journal of Urology, vol. 169, p. 183 (Apr. 2003).

Kettel, L. Michael et al., An Anatomical Evaluation of the Sacrospinous Ligament Colpopexy, Surg. Gynecol. Obstet., 168(4):318-22, Apr. 1989.

Flynn, B.J. et al., Surgical Management of the Apical Vaginal Defect, Curr. Opin. Urol. 12(4):353-58, Jul. 2002.

Buller, J.L. et al., Uterosacral Ligament: Description of Anatomic Relationships to Optimize Sergical Safety, Obstet. Gynecol. 97:873-79, 2001.

Brochure, "GPS for Pelvic Floor Repair," Gynecare Prolift, 6 pages, 2005.

Greene, Frederick, "Repair of Rectal Prolapse Using a Puborectal Sling Procedure,"Arch Surg; vol. 118, pp. 398-401 (Apr. 1983).

Shafik, Ahmed, "Puborectoplasty, New Technique for the Repair of Fecal Incontinence," Dig. Surg. 1991; 8: pp. 182-186.

McMahan et al., Rectal prolapse. An update on the rectal sling procedure,: Am Surg., vol. 53. No. 1, pp. 37-40, 1987.

O'Rourke D. et al., "A puborectal sling in the management of anal incontinence and rectal prolapse," Aust N Z J Surg., vol. 55, No. 5, pp. 493-495, 1985.

O'Rourke D. et al., "An anorectal sling in the treatment of rectal prolapse and incontinence," Aust N Z J Surg:, vol. 44, No. 2, pp. 144-146, 1974.

Kobashi. K.C. et al., "A New Technique for Cystocele Repair and Transvaginal Sling: The Cadaveric Prolapse Repair and Sling (CaPS)," Urology 56 (Supplement 6A), Dec. 2000.

\* cited by examiner

PELVIC FLOOR TREATMENTS AND RELATED TOOLS AND IMPLANTS

PRIORITY CLAIM

This application claims benefit from International Application No. PCT/US2008/009066, which was filed on Jul. 25, 2008, which in turn claims priority to U.S. Provisional Patent Application having Ser. No. 60/952,411, filed on Jul. 27, 2007, titled PELVIC FLOOR TREATMENTS AND ASSOCIATED IMPLANTS; and U.S. Provisional Patent Application having Ser. No. 61/012,260, filed on Dec. 7, 2007, titled PELVIC FLOOR TREATMENTS AND ASSOCIATED IMPLANTS, wherein the entireties of said patent applications are incorporated herein by reference.

FIELD OF THE INVENTION

The invention relates to apparatus and methods for treating pelvic conditions by use of a pelvic implant to support pelvic tissue. The pelvic conditions include conditions of the female or male anatomy, and specifically include treatments of female or male urinary and fecal incontinence, and treatment of female vaginal prolapse conditions including enterocele, rectocele, cystocele, vault prolapse, conditions of the pelvic floor, and any of these conditions in combination. Particular examples of articles and tools described herein include: surgical implants that support pelvic tissue and that are adjustable in terms of their length or tension, during or after being implanted; implants having certain general and specific types of tissue fixation devices, adjusting engagements, or designs (e.g., shapes) that allow placement of extension portions a desired pelvic locations; and tools having various configurations.

BACKGROUND

Pelvic prolapse, including vaginal prolapse, can be caused by the weakening or breakdown of various parts of the pelvic support system, such as the pelvic floor or tissue surrounding the vagina. Due to the lack of support, structures such as the uterus, rectum, bladder, urethra, small intestine, or vagina, may begin to fall out of their normal positions. Prolapse may cause pelvic discomfort and may affect bodily functions such as urination and defecation.

Pelvic prolapse conditions can be treated by various surgical and non-surgical methods. Non-surgical treatments for vaginal prolapse include pelvic muscle exercises, estrogen supplementation, and vaginal pessaries. The Perigee® system, developed by American Medical Systems located in Minnetonka, Minn., is a surgical technique for the repair of anterior vaginal prolapse. Additionally, the Apogee® system, developed by American Medical Systems located in Minnetonka, Minn., is a surgical technique for the repair of vaginal vault prolapse and posterior prolapse.

SUMMARY

In some prolapse surgical techniques, it is desirable to attach the repair material to the ischial spine for more natural support. However, ischial spine attachment is not easily achieved, due to the shallowness of surrounding soft tissue. Another obstacle is the accumulation of tissue into fixation elements, clogging the inside and impeding translational movement. Furthermore, fixation elements are small and not easily managed. The present invention includes teachings to achieve ischial spine support, tools for soft tissue fixation, measures to minimize tissue accumulation in adjusting element s (e.g., grommets or "eyelets"), and concepts for the delivery of fixation elements.

The present disclosure identifies pelvic implants, components of implants, related devices, systems and kits containing these, and methods of using these for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), conditions of the pelvic floor and result from weakness or trauma of pelvic floor muscles such as the levator ("levator ani") or coccygeus muscle (collectively the pelvic floor), and other conditions caused by muscle and ligament weakness.

Exemplary methods can involve treatment of vaginal prolapse, including anterior prolapse, posterior prolapse, or vault prolapse. A method can be transvaginal, involving a single incision in the vaginal tissue, with no external incision.

Certain methods can provide for Level 1 support of the vaginal apex in combination with Level 2 support of medial vaginal sidewall tissue. In terms of vaginal prolapse, Level 1 vaginal tissue support relates to support of the top portion, or "apex" of the vagina. This section of tissue is naturally supported by the cardinal ligament that goes laterally to the ischial spine and crosses over medially to the sacrospinous ligament, and also by the uterosacral ligament that anchors into the sacrum. Level 2 support of vaginal tissue is support of tissue of the mid section of the vagina, below the bladder. This tissue is partially supported by the cardinal ligament but is predominantly supported by lateral fascial attachments to the arcus tendineus or white line. Level 3 support is that of the front end (sometimes referred to as the "distal" section) of the vagina right under the urethra. Natural support includes lateral fascial attachments that anchor into the obturator internus muscle.

One method that can provide a combination of Level 1 and Level 2 support, can involve contacting vaginal sidewall tissue to an arcus tendineus, optionally by placing a segment (e.g., mesh) of implant between tissue of the arcus tendineus and tissue of the vaginal sidewalls. Alternate methods can involve an implant that includes a scaffold portion that extends from a posterior location of the implant to a location at a mid-length or an anterior of the implant. The scaffold connects to the tissue support portion (optionally through an extension portion that extends from a side of the tissue support portion) and these structures support the mid-portion of the urethra, e.g., vaginal sidewalls.

Any implants or methods described can involve tissue fasteners that are designed to secure an implant extension portion or an implant scaffold portion to soft tissue. These may be in the form of a soft tissue anchor, a self-fixating tip, a spring-biased fastener that can insert into tissue or that may grasp and hold tissue, a fastener that includes a male component that engages a female component (e.g., within tissue, or may involve extensions (tines or teeth) that can be extended from a delivery tool to splay laterally into soft tissue.

Implants can include features such as adjusting engagement (one-way or two-way); combinations of a one-way and a two-way adjusting engagement present on a single implant segment (e.g., extension portion piece or segment or scaffold portion piece or segment); scaffold portions as described; multiple pieces. Other embodiments of implants and methods can involve the use of an extension portion piece that includes a mesh portion and a non-mesh portion. These implants and methods may further involve a grommet management tool.

Any implant as described, for use according to any pelvic treatment method, can be placed within a patient by a tool that includes a pore engagement at a length of the shaft, which allows control of a segment of implant that is being manipulated by the tool.

In one aspect, the invention relates to a method for treating vaginal prolapse. The method includes: providing an implant that includes a tissue support portion and two or more extension portions; placing the tissue support portion in contact with vaginal tissue to support the vaginal tissue; extending a posterior extension portion to engage a sacrospinous ligament, and extending a lateral extension portion to engage tissue at a region of ischial spine.

In another aspect, the invention relates to a method for treating vaginal prolapse that includes: providing an implant comprising a tissue support portion and a two or more extension portions, placing the tissue support portion in contact with vaginal tissue to support the vaginal tissue, extending a posterior extension portion to engage a sacrospinous ligament, and extending an anterior extension portion to engage an obturator foramen.

In another aspect the invention relates to a method for treating vaginal prolapse with Level 1 and Level 2 support. The method includes: providing an implant that includes a tissue support portion and two or more extension portions, placing the tissue support portion in contact with vaginal tissue to support the vaginal tissue, extending an extension portion to engage a sacrospinous ligament to provide Level 1 support, and supporting vaginal tissue to provide Level 2 support.

In another aspect the invention relates to a pelvic implant. The pelvic implant includes: a tissue support portion having an anterior end, a posterior end, and right and left sides extending between the anterior end and the posterior end; a first right-side extension portion extending from the right side of the tissue support portion and a first left-side extension portion extending from the left side of the tissue support portion; optionally, a second right-side extension portion extending from a right side of the tissue support portion and optionally a second left-side extension portion extending from the left side of the tissue support portion; a right-side scaffold portion having an anterior end, a posterior end, and a right-side scaffold length between the anterior end and the posterior end, the anterior end connected to the tissue support portion or second right-side extension portion, the right-side scaffold portion being connected to the first right-side extension portion along the right-side scaffold length, and the distal end includes a tissue fastener; a left-side scaffold portion having an anterior end, a posterior end, and a left-side scaffold length between the anterior end and the posterior end, the anterior end connected to the tissue support portion or second left-side extension portion, the left-side scaffold portion being connected to the first left-side extension portion along the left-side scaffold length, and the distal end includes a tissue fastener.

In another aspect the invention relates to a pelvic implant that includes a tissue fastener capable of engaging soft tissue of a pelvic region. The tissue fastener includes spring-biased extensions. The spring-biased extensions include an open configuration and a closed configuration. The tissue fastener can be contacted with tissue when placed in an open configuration, and closed to the closed configuration to grasp the tissue.

In another aspect the invention relates to a pelvic implant that includes a tissue fastener capable of engaging soft tissue of a pelvic region. The tissue fastener includes extensions. The extensions include an open configuration and a closed configuration. The tissue fastener can be contacted with tissue when placed in the closed configuration, and inserted into tissue to achieve an open configuration within the tissue.

In another aspect the invention relates to a kit that includes a pelvic implant. The pelvic implant includes a support portion piece and an extension portion piece. The extension portion piece includes a mesh portion and a non-mesh portion. The support portion piece includes an adjusting engagement capable of adjustably engaging the support portion piece.

In another aspect, the invention relates to an insertion tool that can be used to place a tissue fastener of a pelvic implant. The insertion tool includes a shaft having a pore engagement located along a length of the shaft.

In another aspect, the invention relates to an adjusting tool that includes a shaft and a distal end. The distal end includes a first set of opposing arms. Each set of arms extends laterally from the distal end of shaft to define a slot.

In another aspect the invention relates to a pelvic implant that includes a grommet. The grommet includes an aperture and an aperture extension.

In another aspect the invention relates to a pelvic implant that includes a tissue support portion, a set of two anterior extension portions extending from the tissue support portion, a set of two lateral extension portions extending from the tissue support portion, and a set of two posterior extension portions extending from the tissue support portion. When the tissue support portion is placed to support tissue of a vagina, the anterior extension portions can be connected to opposing obturator foramen, the lateral extension portions can be connected to opposing regions of ischial spine and optionally contacted to tissue of opposing arcus tendineus, and the posterior extension portions can be connected to opposing sacrospinous ligaments.

The following patent documents are incorporated herein by reference: US Patent Publication No. US 2004/0039453 A1; US Patent Publication No. US 2005/0250977 A1; US Patent Publication No. US 2005/0245787 A1; U.S. Pat. Nos. 6,652,450; 6,612,977; 6,802,807; 7,048,682; 6,641,525; 6,911,003; 7,070,556; 6,354,991; 6,896,651; 6,652,449; 6,862,480; 6,712,772; and PCT Application Serial No. Unknown, filed Jun. 15, 2007, titled "Surgical Implants, Tools and Methods for Treating Pelvic Conditions" (Attorney Docket No. AMS-3419-PCT).

Figure 1A:
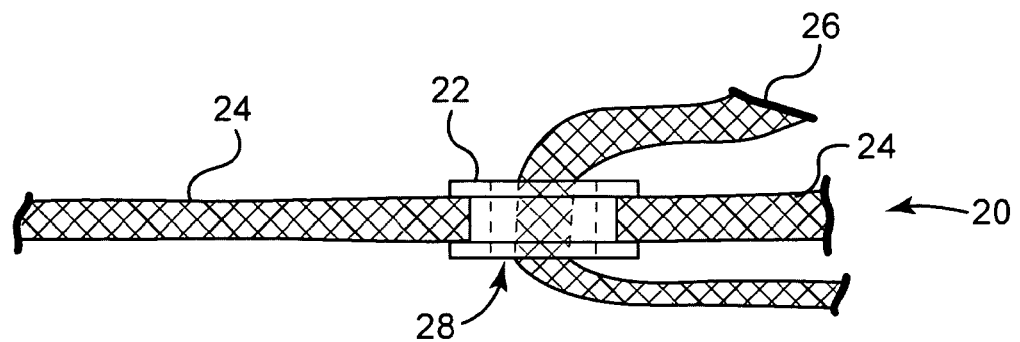
FIGS. 1A and 1B illustrate embodiments of implants.

All drawings are schematic, and not to scale.

DETAILED DESCRIPTION

The following description is meant to be illustrative only and not limiting. Other embodiments of this invention will be apparent to those of ordinary skill in the art in view of this description.

The invention involves surgical instruments, assemblies, and implantable articles for treating pelvic floor disorders such as fecal or urinary incontinence, including stress urinary incontinence (SUI), prolapse, etc. According to various embodiments, a surgical implant can be used to treat a pelvic condition, including the specific examples of surgically placing a pelvic implant to treat a condition such as vaginal prolapse or incontinence (male or female). Described are various features of surgical implants, surgical tools, surgical systems, surgical kits, and surgical methods useful for installing implants. An implant can be implanted in a male or a female patient to treat a condition such as urge incontinence; stress urinary incontinence; mixed incontinence; overflow incontinence; functional incontinence; fecal incontinence; prolapse (e.g. vaginal or uterine); enterocele (e.g. of the uterus); rectocele; cystocele; anatomic hypermobility; conditions of the pelvic floor caused by weakness or trauma of pelvic floor muscles such as the levator ("levator ani") or coccygeus muscle (collectively the pelvic floor); other conditions caused by muscle and ligament weakness; and combinations of these.

An implant can include a tissue support portion that can be used to support pelvic tissue such as the urethra (which includes the bladder neck), bladder, rectum, vaginal tissue (Level 1, Level 2, Level 3, or combinations of these), pelvic floor tissue, etc. During use, the tissue support portion is typically placed in contact with and attached to tissue to be supported, such as by attachment using one or more sutures. An implant can additionally include one or more extension portion attached to the tissue support portion, or one or more scaffold portion attached to a tissue support portion or an extension portion. A tissue fastener or a connector can be included at an end of an extension or scaffold portion.

The tissue support portion is designed to support a specific type of pelvic tissue such as the urethra, bladder, or vaginal tissue (anterior, posterior, apical, etc.), rectum, tissue of the pelvic floor such as levator muscle, etc. The tissue support portion can be sized and shaped to contact the desired tissue when installed, e.g., as a "sling" or "hammock," to contact and support pelvic tissue.

Extension portions are pieces of material, generally elongate or otherwise extended from a tissue support portion, and that are useful to optionally either pass through or attach to tissue of the pelvic region to thereby provide support for the tissue support portion and the supported tissue. One or multiple (e.g., one, two, four, or six) extension portions can extend from a tissue support portion for attachment to tissue in the pelvic region, such as by extending to an internal anchoring point (for attachment by bone anchor, tissue fastener, etc.), or through a tissue path to an external incision.

An implant can optionally include a scaffold portion, (which can be considered a type of extension portion, such as if the scaffold portion extends from a tissue support portion) that can be extended internally within a patient and secured to tissue of a pelvic region or to a location of the implant, and is used to support a tissue support portion or extension portion attached to the scaffold portion along a length of the scaffold portion, between two ends of the scaffold portion. A scaffold portion can have two ends. Either end can be attached internally to tissue of the pelvic region r to the implant, such as to a tissue support portion, another extension portion, or another scaffold portion. An end of a scaffold portion can be securely (non-adjustably) attached to a tissue support portion or another extension portion, such as by a suture, rivet, staple, etc.; may be integrally formed with the tissue support portion or extension portion; or may be adjustably attached to a tissue support portion or an extension portion using an adjusting engagement. A scaffold portion may also optionally include an adjusting engagement along the length of the scaffold portion.

A scaffold portion can be sized or adjusted in size to be sufficiently taut upon placement within a pelvic region to be able to support an extension portion or a tissue support portion of an implant attached along a length of the scaffold portion between the two ends of the scaffold portion. An extension portion of an implant, or a tissue support portion of an implant, can be connected to the scaffold portion either in a secure (non-adjustable) manner such as integrally, by a suture, adhesive, thermal bonding, polymeric rivets, or the like, or in an adjusting manner, using and adjusting engagement.

A "multi-piece" implant refers to an implant that includes a "support portion piece" and one or multiple "extension portion piece" or "scaffold portion piece," as separate pieces of the implant. An extension portion piece or scaffold portion piece can be separate from a support portion piece, and can be connected through one or multiple an adjusting engagements. The support portion piece includes a tissue support portion.

Exemplary implants can be made of materials and may be generally shaped and sized with certain individual features that may be found in previous implants, but can be modified to include features as described herein such as a scaffold portion, an adjusting engagement, any of the various tissue fasteners described herein, multi-piece construction, etc., and can be adapted for use according to methods that are described herein. An implant can have features described in the following exemplary documents: U.S. patent application Ser. No. 10/834,943, filed Apr. 30, 2004; U.S. patent application Ser. No. 10/306,179, filed Nov. 27, 2002; U.S. patent application Ser. No. 11/347,063, filed Feb. 3, 2006; U.S. patent application Ser. No. 11/347,596, filed Feb. 3, 2006; U.S. patent application Ser. No. 11/347,553, filed Feb. 3, 2006; U.S. patent application Ser. No. 11/347,047, filed Feb. 3, 2006; U.S. patent application Ser. No. 11/346,750, filed Feb. 3, 2006; U.S. patent application Ser. No. 11/398,368, filed Apr. 5, 2005; U.S. patent application Ser. No. 11/243,802, filed Oct. 5, 2005; U.S. patent application Ser. No. 10/840,646, filed May 7, 2004; and International patent application number PCT/US2006/028828, having an International Filing Date of Jul. 25, 2006; International Application No. PCT/US2007/004015 entitled "SURGICAL ARTICLES AND METHODS FOR TREATING PELVIC CONDITIONS," filed Feb. 16, 2007; International Application No. PCT/US2007/016760 entitled "SURGICAL ARTICLES AND METHODS FOR TREATING PELVIC CONDI- TIONS," filed Jul. 25, 2007; and International Application No. PCT/US2008/000033 entitled "METHODS FOR INSTALLING SLING TO TREAT FECAL INCONTINENCE, AND RELATED DEVICES," filed Jan. 3, 2008; the entireties of each of these disclosures being incorporated herein by reference.

Examples of commercial implants include those sold by American Medical Systems, Inc., of Minnetonka Minn., under the trade names Apogee®, Perigee®, and Elevate™ for use in treating pelvic prolapse (including vaginal vault prolapse, cystocele, enterocele, etc.), and Sparc®, Bioarc®, Monarc®, and MiniArc™ for treating urinary incontinence. Implants useful according to the present description can include one or more features of these commercial implants.

An implant may include portions, pieces, or segments, that are synthetic or of biological material (e.g., porcine, cadaveric, etc.). Extension portions and scaffold portions (made of a single piece or of more than one piece) may be, e.g., a synthetic mesh such as a polypropylene mesh. A tissue support portion may be synthetic (e.g., a polypropylene mesh) or biologic. (As used herein, the term "portion of implant" (or "implant portion") refers generally to any piece, segment, or portion (e.g., extension portion or scaffold portion) of an implant. The term "segment of implant" (or "implant segment") refers to an elongate length of implant material, such as a length of an elongate section of an extension portion or a scaffold portion.)

Examples of implants for treating vaginal prolapse (e.g., anterior vaginal prolapse, posterior vaginal prolapse, vaginal vault prolapse) can include a central support portion and from two to four to six extension portions, and may take the form of an integral piece of mesh or other implant material, or multiple pieces of mesh or other implant material attached in a modular fashion. See, e.g., Assignee's copending U.S. patent application Ser. Nos. 11/398,369; 10/834,943; 11/243,802; 10/840,646; PCT/2006/028828; among others. Particularly useful examples of implants for treating vaginal prolapse, using any one or a combination of devices or methods as described herein can be implants described in Assignee's copending International Patent Application No. PCT/US2007/014120, entitled "SURGICAL IMPLANTS, TOOLS, AND METHODS FOR TREATING PELVIC CONDITIONS," filed Jun. 15, 2007, the entirety of which is incorporated herein by reference.

According to various embodiments of implants described herein, an implant can include pieces or portions that are adjustably connected together by an adjusting engagement, which may be either a one-way adjusting engagement or a two-way adjusting engagement, to allow a portion or a segment of an implant to be moved relative to another portion or segment, and adjusted as to length, tension, or positioning. As an example, an extension portion piece can be attached to a support portion piece at an adjusting engagement to allow adjustment of a length of extension portion. Alternately or in addition, a scaffold portion or scaffold portion piece can be attached to a support portion piece or to an extension portion at an adjusting engagement to allow adjustment of length or tension of a scaffold portion.

Some adjusting engagements can allow free two-way movement of one piece relative to another piece (e.g., a "two-way" adjusting engagement). This type of adjusting engagement allows easy movement of a segment of implant in two directions through an adjusting engagement. The force needed to move the segment of implant in one direction is substantially equal to the force needed to move the segment in the opposite direction, and, preferably, the two-way adjusting engagement does not substantially hinder the movement of a segment of implant through the adjusting engagement with frictional surfaces such as extensions (e.g., "teeth") extending into an aperture through which the segment of implant is moved. As an example, a two-way adjusting engagement may include an open (smooth) aperture that may be circular, oval, elongate such as in the form of a slit or slot, etc. The aperture may optionally be reinforced by a reinforcement of a shape that is similar to the aperture, such as by a fabric or a polymeric material such as a grommet (e.g., a "loose grommet" or "eyelet"), which may be circular, or may be of another shape. The reinforcement (e.g., grommet) defines a reinforced aperture through which a segment of implant can pass relatively freely and with the same resistance two different directions.

Other adjusting engagements may allow for one-way adjustment such as shortening of a length of the extension portion or scaffold portion. These adjusting engagements can be referred to as "one-way" adjusting engagements, and allow adjustment of a length of an implant portion in one direction and not in an opposite direction. An exemplary one-way adjusting engagement can include an aperture through which a segment of implant can extend, and one or multiple surfaces (e.g., extensions or teeth) that frictionally engage the segment of implant, e.g., by extending into or toward the aperture or otherwise contacting the segment of implant to inhibit movement of the segment of implant relative to the adjusting engagement. The one-way engagement can preferentially allow movement of the segment of implant through the aperture in one direction while inhibiting movement of the segment of implant in an opposing direction.

Still other embodiments of adjusting engagements may allow for two-way adjustment of a length of extension portion in one configuration (an "open" configuration), and further include a structure or mechanism that can be switched, activated, moved, removed, closed, or opened, to secure a frictional adjusting engagement at a selected location to prevent movement in either direction.

FIGS. 1A, 1B, 2A, and 2B illustrate various embodiments of adjusting engagements in the form of grommets.

Figure 1B:
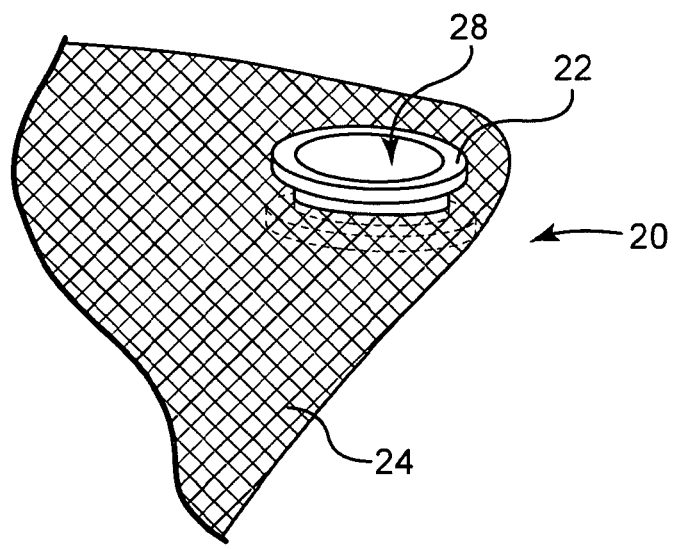

FIGS. 1A and 1B show implant 20 that includes implant portion 24 (e.g., a tissue support portion or a support portion piece), and grommet 22, which is a two-way, non-frictional adjusting engagement, sometimes referred to as an "eyelet" or a "loose eyelet." Grommet 22 includes aperture 28, through which implant segment 26 can pass freely in two directions, to adjust lengths of implant portions extending from either side of grommet 22.

Figure 2A:
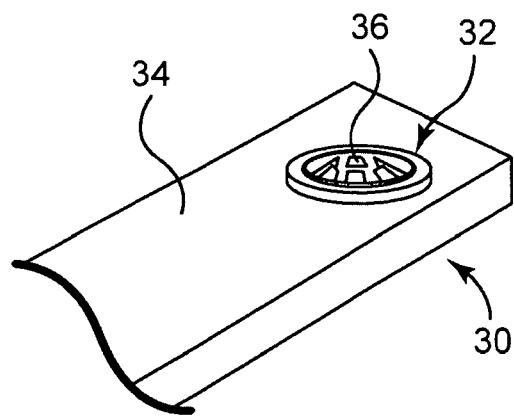
FIGS. 2A and 2B illustrate embodiments of implants and adjusting engagements.
Figure 2B:
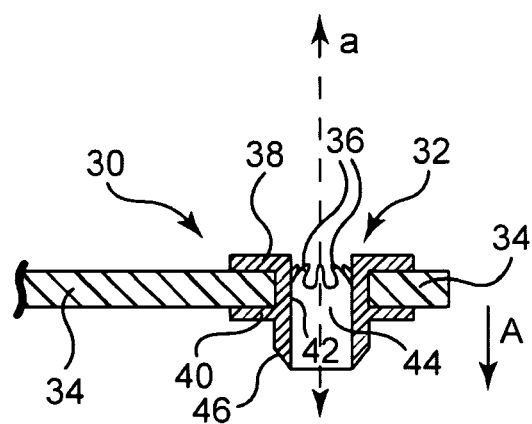

FIG. 2A shows a perspective view of implant 30 with one-way frictional adjusting engagement 32 attached to a portion of implant 34. FIG. 2B is a cross-sectional view. As shown, one-way, frictional, adjusting engagement 32 includes central aperture 44, first flange 40, second flange 38, and a plurality of extensions (flaps or "teeth") 36 extending in the direction of aperture 44 or an longitudinal axis ("a") extending through aperture 44. In an exemplary embodiment, the outside diameter of frictional adjusting engagement 32 can be about 5 mm (e.g., from 3 to 10 millimeters) and the length of an extension 36 can be in the range of from about 1 mm to about 2 mm. Aperture extension 46 extends away from flange 40 in a direction (designated "A") in which grommet 32 will be pushed along a length of an implant portion. Grommet 32, a "one-way" adjusting engagement, is able to freely move along an implant portion in direction A, and extensions 36 prevent movement in the opposite direction. An aperture extension 46 can also be useful on a two-way grommet.

Aperture extension 46 is an optional feature of a grommet that is designed to prevent tissue from entering aperture 44 and becoming lodged inside of grommet 32 during movement of grommet 32 along an implant portion. For instance, when implant portion 34 is moved within a patient, in direction A, relative to an implant portion (not shown) extending through aperture 44, tissue may come into contact with the implant portion (which may be a mesh) and with grommet 32. Absent aperture extension 46, the tissue can tend to be forced into aperture 44. This can be especially true if the implant portion extending through aperture 44 is made of mesh. Aperture extension 46 deflects and blocks tissue from entering aperture 44. An exemplary length of extension 46 (the distance from flange 40 to the far tip of aperture extension 46) can be a length that is approximately the same as the thickness of grommet 32 from flange 38 to flange 40 (including opposing the width of the flanges). Exemplary thicknesses can be, e.g., from 1 to 5 millimeters, e.g., from 2 to 4 millimeters.

In particular embodiments of implants, an implant segment may engage a separate implant segment or portion of implant at an adjusting engagement, and another adjusting engagement can be used to secure final positioning of the two portions of implant. As an example, a segment of an extension portion piece may extend through a two-way adjusting engagement located at a support portion piece. A segment of the extension portion piece (alternately a scaffold portion piece) extending from one side of the two-way adjusting engagement can be useful to form an extension portion (alternately scaffold portion) of adjustable length; an end of this segment away from the adjusting engagement can include a tissue fastener for fastening to soft tissue. A second segment of the piece extending from the adjusting engagement, on the opposite side of the two-way adjusting engagement, can be referred to as a loose end; this end may be cut as desired or attached to pelvic anatomy as desired.

Because the two-way adjusting engagement allows adjustment in two directions, a second adjusting element can be used to fix the extension portion piece in place relative to the support portion piece. For example, an adjusting engagement in the form of a one-way grommet can be placed on the loose end of the extension portion piece. The one-way grommet may be used to secure the positioning of the extension portion piece and support portion piece after adjustment.

In use, the tissue fastener at one end of the extension portion is placed at tissue as desired, and the second (loose) end of the extension portion piece is passed through the two-way adjusting engagement. The engagement is adjusted to place the support portion piece at a desired position (length) of the extension portion piece. A second adjusting engagement, e.g., a one-way grommet, is slid onto the loose end of the extension portion piece and slid along the extension portion piece to a location at the two-way adjusting engagement. The one-way adjusting engagement moves easily along the extension portion piece in the direction toward two-way adjusting engagement, and does not move easily in the opposite direction. Once placed in position near the two-way adjusting engagement of the support portion piece, the support portion piece is prevented from moving along the extension portion piece in the direction of the one-way adjusting engagement.

Implants as described can include a tissue fastener at a distal end of an extension portion, which is the end not attached to a tissue support portion. (The term "distal" as used herein may refer to an end of a structure that is "away from" a different structure, such as a distal end of an extension portion that is the end away from a connection to a tissue support portion. The term "distal" may also (based on arbitrary selection) generally refer to a location that is relatively more posterior to a patient, and relatively farther away from a surgeon performing a method as described; "proximal" generally refers to a location that is relatively more anterior to a patient, and relatively closer to a surgeon performing a method as described. Any other convention, such as an opposite convention, could alternately be used to refer to features of devices and methods as described.)

A tissue fastener can be of various types, including, as examples, a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007, the entirety of which is incorporated herein by reference.) An implant may also have extension portions that do not include a tissue fastener at a distal end, for example if the distal end is designed to be secured to tissue by other methods (e.g., suturing), or is intended to pass through an external incision, in which case the extension portion may include a connector, dilator, or dilating connector, which connects to an elongate tool that can be used to either push or pull the connector, dilator, or dilating connector through a tissue path to an external incision.

A tissue fastener can be placed at and secured within internal tissue of the pelvic region to support the implant and pelvic tissue that is supported by the implant. A tissue fastener can be placed at muscle tissue of an obturator foramen (e.g., obturator internus muscle), tissue of an arcus tendineus or surrounding an arcus tendineus, tissue of a sacrospinous ligament, tissue in a region of a sacrospinous ligament, tissue of a coccyx region, tissue of a region of an ischial spine, tissue of coccygeous muscle, tissue of iliococcygeous muscle, tissue of a uterosacral ligament, tissue of levator muscle, or at other tissue of the pelvic region.

One embodiment of a tissue fastener is a self-fixating tip. A "self-fixating tip" in general can be a structure (sometimes referred to as a soft tissue anchor) connected to an extension portion that can be implanted into tissue (e.g., muscle tissue, tendon tissue, or ligament tissue) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through an incision to reach the interior of the pelvic region. The self-fixating tip may engage the insertion tool at an internal channel of the self-fixating tip, at an external location such as at a base, or at a lateral extension, as desired.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/ 004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion (also meaning, as used herein, a scaffold portion). The base extends from the proximal base end to the distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient. Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

Figure 3A:
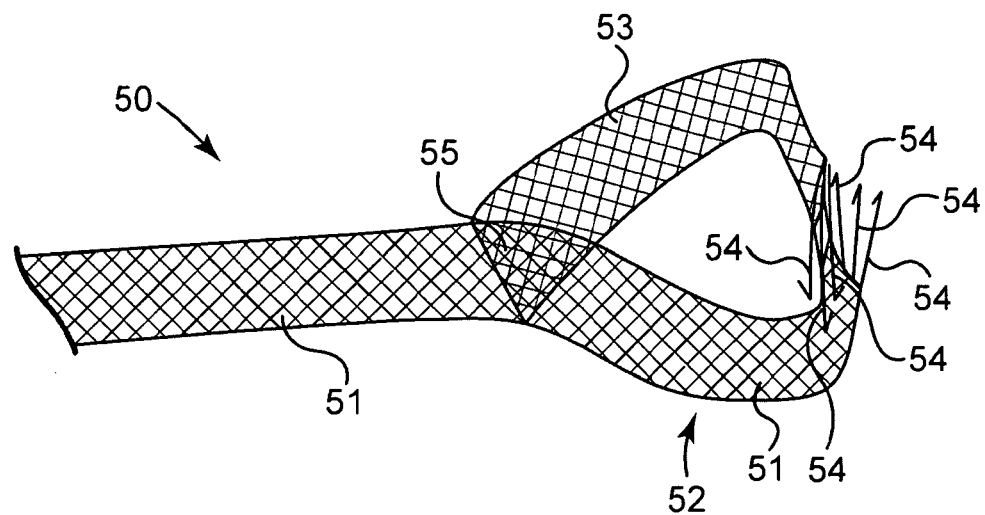
FIGS. 3A and 3B illustrate embodiments of implants, tissue fasteners, and insertion tools.

Another form of useful tissue fastener is the type that includes opposing male and female features that engage each other in a secure manner, preferably by being inserted into tissue from different directions to "bite" or "pinch" the tissue and contact each other within the tissue. FIG. 3A shows an embodiment of tissue fastener that includes opposing male and female features that can be engaged and connected when brought into contact with each other, within tissue, especially soft tissue such as muscle, ligament, tendon, etc. Implant 50 includes a tissue fastener for placing a distal end of an extension portion at tissue of the pelvic region. Distal end 52 of a portion of implant, e.g., an extension portion or a scaffold portion, includes continuous base portion 51 and branch 53 connected along seam 55 to form "Y-shaped" distal end 52. Pluralities (only one is required) of male connector elements 54 in the form of elongate barbed members (e.g., barbed "fingers") extend from each distal end of base portion 51 and branch 53. Apertures of the material of the of Y-shaped distal end 52 base portion 51 and branch 53 (e.g., mesh) function as female connector elements into which the barbed ends of fingers 54 become engaged when the two opposing ends of the Y-shaped distal end are pushed to contact each other. Barbed fingers 54 are sized and prepared from materials that allow the barbed ends of fingers 54 to penetrate tissue of the pelvic region, such as muscle, ligament, tendon, etc., and also to engage apertures of material of the Y-shaped distal end. FIG. 3A shows fingers 54 located at both a distal end of base 51 and a distal end of branch 53. In alternate embodiments, fingers may be present at only one of these distal ends, and not the other.

Figure 3B:
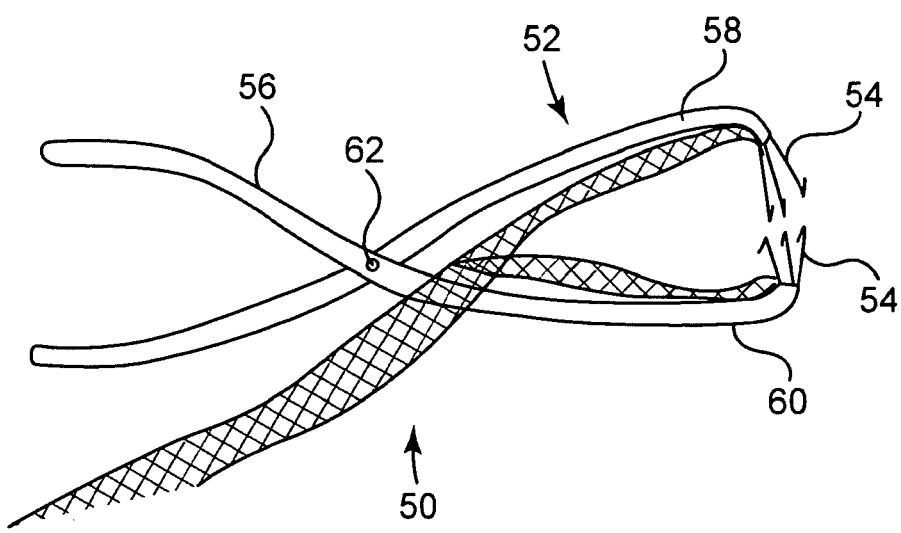

FIG. 3B illustrates an installation tool, tool 56, for installing implant 50. Installation tool 56 includes jaws 58 and 60 that pivot about pivot point 62. Jaws 58 and 60 include structure to engage each distal end of the base and branch of Y-shaped distal end 52 to hold male connector elements 54 for placement into tissue in a manner to engage tissue and to also engage the opposing mesh of Y-shaped distal end 52. In use, jaws 58 and 60 are positioned at a desired tissue location, with a piece of tissue placed (or pinched") between opposing male connector elements 54. Tool 52 is then used to drive opposing male connector elements 54 toward each other, through tissue, and into engagement within opposing mesh. Such action will bite or clamp a portion of tissue between Y-shaped distal end 52 of implant 50, for securing implant 50 in position. FIG. 3B shows fingers 54 located at both a distal end of base 51 and a distal end of branch 53. In alternate embodiments, fingers may be present at only one of these distal ends, and not the other.

Figure 4A:
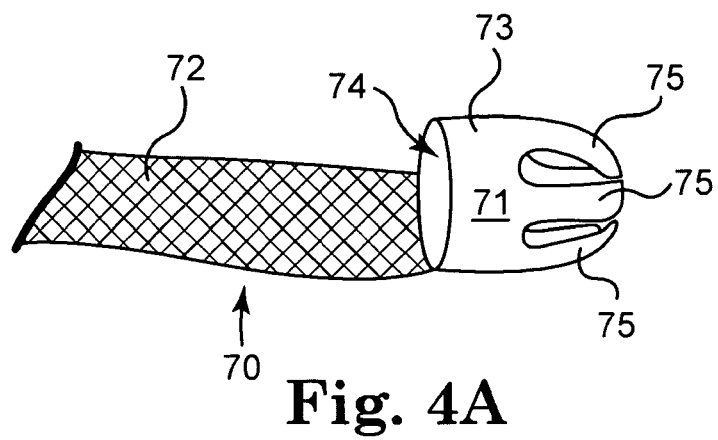
FIGS. 4A, 4B, and 4C illustrate embodiments of implants, tissue fasteners, and insertion tools.
Figure 4B:
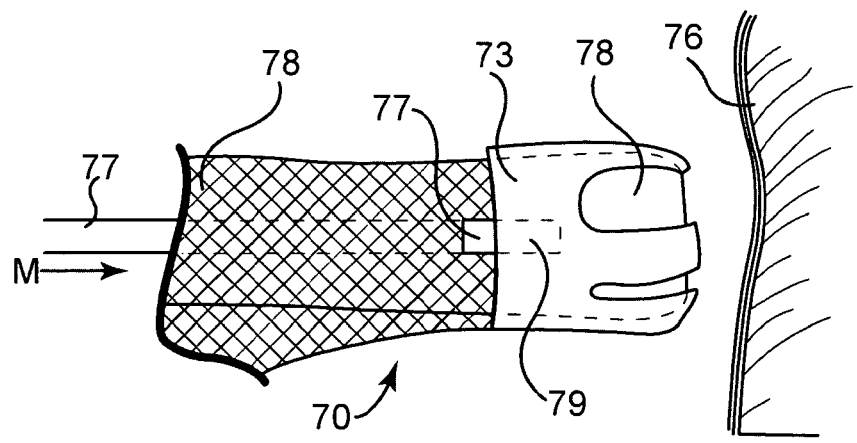
Figure 4C:
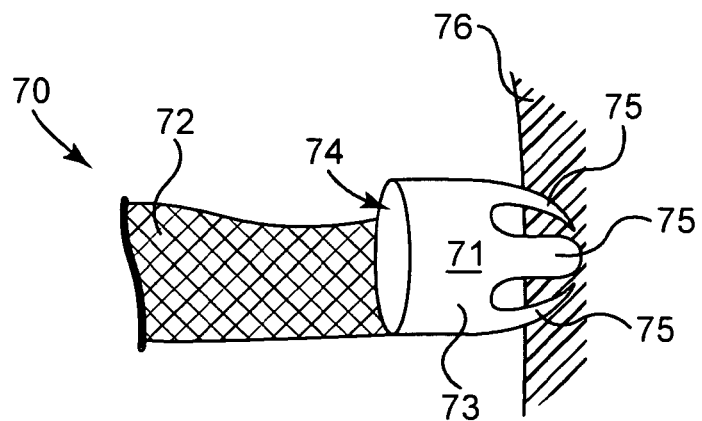

FIGS. 4A, 4B, and 4C illustrate another example of a tissue fastener. Tissue fastener 73 is an integral, spring-biased tissue fastener that can exhibit an opened configuration and a closed configuration. As shown at FIG. 4A, tissue fastener 73 is attached to a distal end of implant portion 72, such as an extension portion or a scaffold portion. Cylindrical body 71 includes aperture 74 on a proximal end, the proximal end being attached to a distal end of implant portion 72. On a distal side of body 71 are spring-biased, curved prongs (e.g., teeth, tines, extensions, etc.) that are shaped to penetrate tissue of a pelvic region. For instance, prongs 75 may have sharpened edges or ends and dimensions to extend a desired depth into tissue. Prongs 75 are spring-biased toward the closed configuration illustrated at FIG. 4A.

Still referring to FIGS. 4A, 4B, and 4C, prongs 75 can be opened or expanded as shown at FIG. 4B, to become spring-loaded, by inserting an end of an inserting tool 78, into aperture 74 and pushing the end of the inserting tool against prongs 75, causing prongs 75 to splay apart to the opened configuration. In the opened (spring-loaded) configuration shown at FIG. 4B, tissue fastener 73 can be placed with ends of prongs against soft tissue of a pelvic region. Tissue fastener 73 can be pushed from the end of inserter tool 78 by any mechanism, such as by a pushing mechanism 77. Pushing mechanism 77 moves in direction M, within slot. 79, and a surface of pushing mechanism 77 engages a surface of tissue fastener 73, to allow fastener 73 to be pushed from a distal end of inserter tool 78. When pushed from inserter tool 78, with prongs 75 in contact with a surface of tissue, prongs 75 contact and sink into tissue, grabbing the tissue between prongs 75 and securing tissue fastener 73 to tissue 76, as shown at FIG. 4C.

Figure 5A:
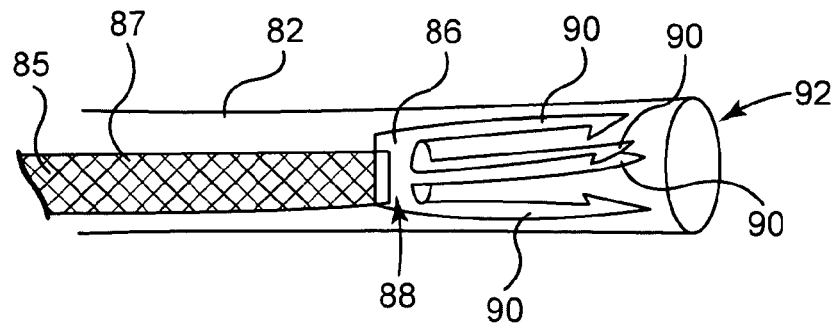
FIGS. 5A, 5B, and 5C illustrate embodiments of implants, tissue fasteners; and insertion tools.
Figure 5B:
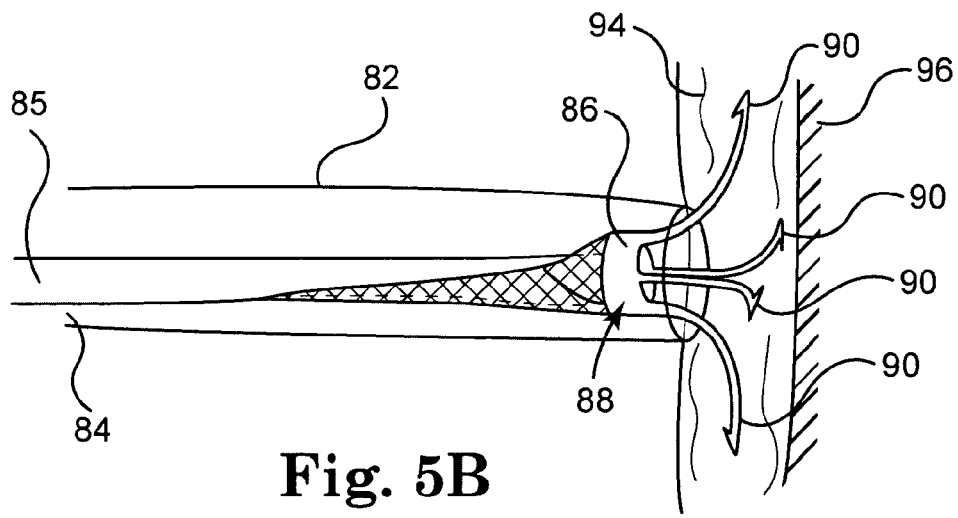
Figure 5C:
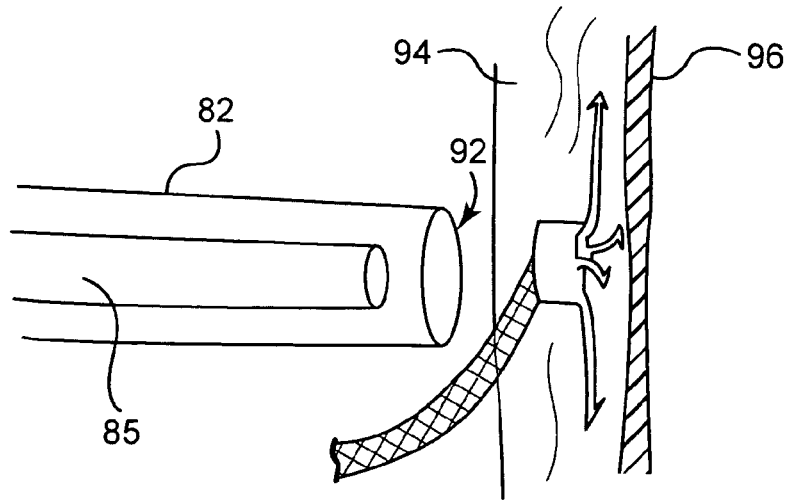

FIGS. 5A, 5B, and 5C illustrate another example of a tissue fastener. Tissue fastener 86 is shown at FIG. 5A in a closed position, when loaded in a tube at a distal end of insertion tool 82. Tissue fastener 86 includes body 88 and projections (or "arms") 90, which can be inserted into tissue of a pelvic region. Tissue fastener 86 is attached to a distal end of implant portion 84 (e.g., an extension portion or a scaffold portion), also located within a hollow body of a distal end of insertion tool 82 (illustrated in cross section). Pusher 85 includes a moveable shaft that is capable of moving within insertion tool 82 to push tissue fastener 86 out of aperture 92 at the distal end of insertion tool 82. Projections 90 can be spring-biased to spread (e.g., splay) apart and at a direction that includes a lateral component, automatically when extended from aperture 92. In alternate embodiments, distal end of insertion tool 82 can include a mechanism such as a deflecting surface (not shown) that can cause projections 90 to deflect sideways upon entry into tissue 94. In yet another embodiment, projections 90 may become spread by being deflected by tissue such as bone 96, located behind tissue 94, which may be soft tissue such as muscle, ligament, tendon, fascia, or the like. These figures show fastener 86 as including four projections (90); more or fewer can also be used as desired. Preferably, projections of a tissue fastener as described and illustrated can be inserted into tissue and splay to cover an area within the tissue, without passing through the tissue, and remaining in the layer of tissue as the projections extend away from the insertion.

A tissue fastener such as fastener 86 can desirably produce a relatively small entry opening into tissue and can splay to extend projections 90 across an area having a diameter in the range from 1 to 3 centimeters. A small entry opening, and the ability to be secured to soft tissue, can allow for placement of projections 90 at a location at a region of an ischial spine. Projections 90 can include a barb, as illustrated, or may include other frictional surfaces, such as multiple barbs per projection; apertures to grasp tissue; sharp or jagged edges or teeth along edges; etc. A projection (90) can be made of any suitable material, such as plastic (e.g., polypropylene), steel, stainless steel, Nitinol, etc.

Embodiments of implants and kits according to the present description can include extension portion pieces, as described, of various constructions. Generally, an extension portion piece can include a segment (referred to herein as a "mesh portion," but not necessarily of mesh) having a tissue fastener at one end. The extension portion piece is configured to engage a support portion piece in a manner that allows the mesh portion to provide a structure that includes an extension portion having an adjustable length. An end of the extension portion piece can be placed through an adjusting engagement of a support portion piece, and the end of the support portion piece that includes the tissue fastener forms an extension portion between tissue (with which the tissue fastener becomes engaged) and the support portion piece (to which the extension portion is engaged at the adjustable engagement). The end (segment) of the extension portion piece extending in the other direction, i.e., the end (segment) that does not include the tissue fastener (sometimes referred to as a "loose" end), may be functional as shown at FIGS. 11A, 11B, 12, 13A, and 13B. Alternately, the loose end may be cut after a desired length of the extension portion is achieved.

Embodiments of extension portion pieces used with methods and implants described herein, may also include a non-mesh portion. A non-mesh portion may be, for example a suture, a set of sutures, a tape, or processed (e.g., melted or compressed) mesh. A non-mesh portion can facilitate placement or movement of an extension portion piece relative to a support portion piece, e.g., through an adjusting engagement. A mesh of an extension portion piece may be unwieldy for placing into an adjusting engagement such as a small-diameter grommet, small-dimension slot, toothed-slot, etc. A non-mesh portion can allow easier placement (threading) of an end of an extension portion piece through an aperture of an adjusting engagement by providing a less wieldy, integral (non-mesh), more easily managed end. A non-mesh tape, for example, may be more easily inserted into a slot or a toothed-slot of a one-way or a two-way adjusting engagement. A cylindrical non-mesh portion such as a flexible yet rigid plastic "rod" may be more easily inserted into a round aperture such as an aperture of a grommet, compared to a loose end of a mesh material.

A non-mesh portion may allow for easier adjustment of the extension portion piece within an adjusting element. A non-mesh can exhibit reduced cross section, and friction, relative to a mesh material. Additionally, an extension portion piece made of a full length of mesh material can undesirably engage tissue that can stick to mesh and become lodged in an adjusting element. A non-mesh portion can be less prone to sticking to tissue during use.

Mesh and non-mesh portions of an extension portion piece can be dimensioned to allow the mesh portion to engage an adjusting engagement, when adjusted to a desired length, and when a distal end tissue fastener is fastened to tissue as desired. A non-mesh portion can be of a length to allow manipulation and adjustment of the extension portion piece. Exemplary lengths of a total extension portion piece can be in the range from 4 to 10 inches, including a mesh portion and a non-mesh portion (if present). For an extension portion piece that includes a mesh portion and a non-mesh portion, a mesh portion can be, for example, from 1 to 4 inches in length and a non-mesh portion (e.g., polymeric rod, suture, etc.) can be, for example, from 3.5 to 5.5 inches in length.

Figure 6A:
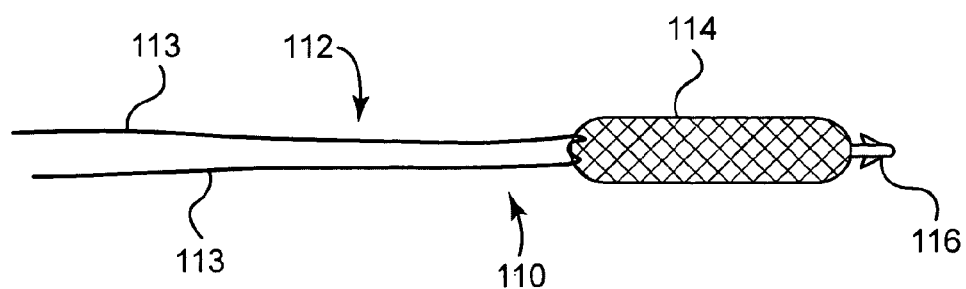
FIGS. 6A, 6B, 6C, and 6D illustrate embodiments of extension portion pieces and grommet management tools.

FIG. 6A illustrates an example of an extension portion piece that includes a mesh portion and a non-mesh portion. Extension portion piece 110 includes mesh portion 114 and non-mesh portion 112, in the form of two sutures 113. Tissue fastener (e.g., a self-fixating tip) 116 is attached to a distal end of mesh portion 114. Sutures 113 are attached to a proximal end of mesh portion 114, such as by knots. Non-mesh portion 112 is illustrated to be in the form of two sutures, but may alternately by more or fewer sutures, such as one suture, or three sutures, optionally tied or braided. Still alternate forms of non-mesh portion 112 may be a polymeric tape, a narrow fabric, or the like, any of which can be selected to be easily threaded through an aperture of a desired adjusting engagement.

Figure 6B:
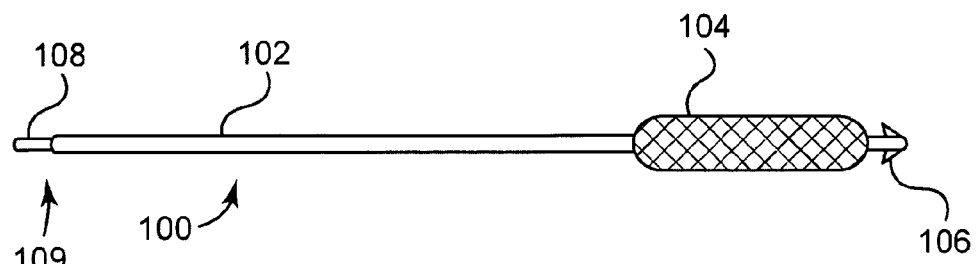

FIG. 6B illustrates another example of an extension portion piece that includes a mesh portion and a non-mesh portion. Extension portion piece 100 includes mesh portion 104 and non-mesh portion 102. Tissue fastener (e.g., self-fixating tip) 106 is attached to a distal end of mesh portion 104. Polymeric (e.g., polypropylene) rod 102 is attached to (preferably integral to) a proximal end of mesh portion 104. Polymeric rod 102 can be formed by any method and may be integrally attached to mesh portion 104, or attached by any technique. As an example, polymeric rod 102 may be prepared by starting with a length of mesh material that is integral to mesh portion 104. The length of mesh can be heat treated at a desired melting temperature (according to the type of polymer of the mesh) to melt the mesh into a polymeric rod having stiff yet flexible mechanical properties. For polypropylene, a desired heat-treating temperature may be in the range from 450 to 520 degrees Fahrenheit. Polymeric rod 102 can be of useful dimensions, such as a length in the range of about 3.5 to 5.5 inches and a width dimension (e.g., diameter) useful to engage a dilator, e.g., about 1/16 of an inch, or from about 1 to 4 millimeters.

Optionally, and as illustrated at FIG. 6B, proximal end 109 of polymeric rod 102 can be shaped to accept or matingly engage an end of a grommet-management tool, such as a polymeric rod, that can facilitate placement of a grommet or other adjusting engagement onto a proximal end of a non-mesh portion of an extension portion piece. Absent some type of grommet-management tool, a user of an extension portion piece such as extension portion piece 100, may place a grommet (e.g., a one-way grommet) onto a proximal end of a non-mesh portion by hand, using fingers. This can be clumsy, especially in potentially confined or deep locations of a pelvic region. A grommet management tool holds one or multiple grommets. An end of the grommet management tool can engage a proximal end of a non-mesh portion of an extension portion piece in a manner to allow the end of the grommet management tool to align and mate against the proximal end of the extension portion piece. Once the ends are engaged, a grommet can slide from the grommet management tool, directly onto the proximal end of the non-mesh portion of the extension portion piece.

A grommet management tool may contain a single grommet, or multiple grommets, and can be used to transfer the one or multiple grommets onto multiple different extension portion pieces of a single or multiple pelvic implants. Advantageously, a grommet management tool can ensure that control of a grommet (or other adjusting engagement) and a location of a grommet are not lost during a surgical procedure, and a grommet can be prevented from becoming a free-standing, separate piece with the potential of becoming lost during a surgical procedure.

Figure 6C:
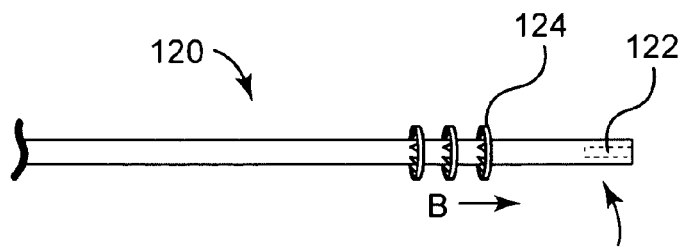

FIG. 6C illustrates grommet management tool 120, which is a rod, such as a polymeric (e.g., polypropylene) rod with a diameter that matches a diameter of polymeric rod 102. One-way (alternately two-way) grommets 124 are aligned along a length of grommet management tool 120. Distal end 124 includes channel or bore 122 that is complementary to cylindrical extension 108 at proximal end 109 of extension portion piece 100. These complementary surfaces can be engaged to allow transfer of a grommet from tool 120 to distal end 124.

In use, non-mesh portion 102 of extension portion piece 100 can be passed through an adjusting engagement of an implant. The implant and extension portion piece can be manipulated and placed as desired, such as at locations within a pelvic region. Channel 122 of grommet management tool 120 can be placed over cylindrical extension 108, and a grommet 124 can be slid in direction B (see FIG. 6C) and transferred from grommet management tool 120 onto proximal end 109 of extension portion piece 100. One-way grommets 124 move easily along an extension portion piece in direction B, and are inhibited from moving in a direction opposite of direction B when placed on a mesh portion such as mesh portion 104. Once placed onto extension portion piece 100, grommet 124 can slide to engage mesh portion 104, and contact the adjusting engagement of the tissue support portion or support portion piece, to secure a relative position of mesh portion 104 to the tissue support portion or support portion piece, e.g., to fix a length of an extension portion of mesh portion 104.

A grommet management tool such as tool 120 can be made of a plastic. metal, or other useful material. As an example, a grommet management tool can be prepared in the same manner used to make a polymeric rod non-mesh portion 102, such as by melting a length of mesh and molding to form a polymeric rod. Other methods can also be used, such as by extruding, injecting molding, etc.

As illustrated, the engagement between distal end 124 of grommet management tool 120, and proximal end 109 of non-mesh portion 102, includes complementary cylindrical surfaces. Other engagements can also be useful, such as complementary conical surfaces, square surfaces, etc.

Optionally, a feature of a non-mesh portion of an extension portion piece, or of a grommet management tool, may include a feature that allows a one-way grommet to pass, only if the one-way grommet is correctly oriented for movement in a desired direction. An example of this feature can be a shoulder or notch located at a proximal end of a non-mesh portion of an extension portion piece (or, alternately, at a distal end of a grommet management tool).

Figure 6D:
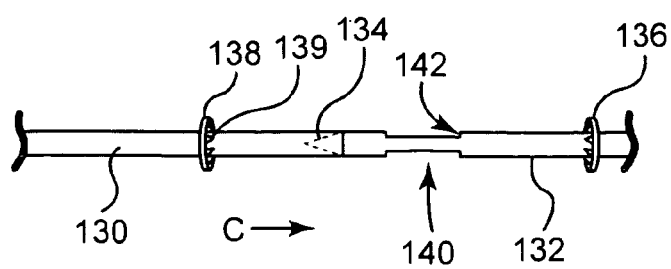

Referring to FIG. 6D, grommet management tool 130 engages proximal end 132 of an extension portion piece. The engagement includes at complementary conical surfaces 134 to allow alignment and mating between the two ends: Notch 140 and shoulder 142 allow one-way grommet 136 to transfer from tool 130 onto non-mesh portion 132, because grommet 136 is oriented in a direction to allow movement in direction C and inhibit movement in a direction opposite of direction C. Notch 140 and shoulder 142 prevent one-way grommet 138 from transferring onto non-mesh portion 132. Grommet 138 is oriented in a direction to allow movement in the direction opposite of direction C and not in direction C. Teeth 139 of grommet 138 would engage shoulder 142 and stop grommet 138 from moving past shoulder 142 in direction C. Notch 140 and shoulder 142 are illustrated to be located on non-mesh portion 132, but alternately could be included on grommet management tool 130.

The implants described can be implanted into a patient by use of various different types of surgical tools, including insertion tools, which generally are tools useful to engage and place a tissue fastener or a connector that is secured to an extension portion (or, as described herein, a scaffold portion) of an implant. Various types of insertion tools are known, and these types of tools and modifications thereof can be used according to the present description to install an implant.

Examples of useful insertion tools include those types of tool that generally include a thin elongate shaft (e.g., needle); a handle attached to one end (a proximal end) of the shaft; and an optional distal end (or "tip") of the shaft adapted to engage an end of an extension portion or scaffold portion, e.g., at a connector or a tissue fastener (e.g., a self-fixating tip). The needle can facilitate placement of the distal end of the extension or scaffold portion at a desired anatomical location that may be internal or through a tissue path to an external incision.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; and PCT application number 2006/0260618; each of which is incorporated herein by reference. Tools described in these patent documents are designed for placement of an implant in a pelvic region for the treatment of prolapse, male or female incontinence, etc.

Exemplary insertion tools can be similar to or can include features of tools described in the above-referenced patent documents. For use according to certain methods described herein, those insertion tools may be modified, such as to allow the insertion tool to be used to place a self-fixating tip through a vaginal or a medial incision, to engage tissue within the pelvic region. The insertion tool can be designed, shaped, and sized, to include an elongate shaft that may be straight or that may be curved in two or three dimensions, that can be inserted through a vaginal incision (for female anatomy) or through a perineal incision (for male anatomy), and extend from that incision to or through pelvic tissue for placement of a distal end of an extension portion.

An example of an insertion tool for use in implanting a pelvic implant, such as by methods as described, can include a handle, a shaft, a distal end of the shaft that engages a tissue fastener (e.g., self-fixating tip), and a pore engagement at a location along a length of the shaft. The pore engagement engages an aperture of a portion of implant, e.g., an aperture of mesh of an extension portion or a scaffold portion. The pore engagement engages a pore of the implant portion in a manner that temporarily fixes the portion of implant against the shaft. The pore engagement can be a small extension, bump, hook, or tang, that extends from the shaft, and that is stationary or moveable (e.g., by movement of an actuator at a proximal end of the tool. The pore engagement can be at any useful location along a length of the shaft, and can preferably be located at a surface of an outer major bend of a curved or angled shaft. A pore engagement can be of a size that engages an aperture of a portion of implant, and can be located to allow the portion of implant to remain taut during insertion. This can be particularly useful if the tissue fastener loosely engages a tip of the shaft by a relatively loose (non-frictional) engagement, such by complementary cylindrical engagement surfaces that do not include a snap-fit, detent, threads, or other frictional feature that maintains the engagement. An example of such a relatively loose engagement is an engagement between a cylindrical tip of an insertion tool and a cylindrical aperture or bore of a base of a self-fixating tip. Temporarily fixing the portion of implant against the shaft can allow a user to better manage the portion of implant during delivery and placement of a tissue fastener.

The pore engagement can be located along the shaft at any distance from the distal end (or tip) of the shaft, and may be located at a distance that is approximately equidistant from distal and proximal ends of the shaft, such as at the medial ⅓ of the length of the shaft, or at a location that is between 30 and 70 (e.g., between 40 and 60) percent of the distance between the proximal end to the distal end. Alternately, the pore engagement may be located at a distance that is approximately 2 to 10 inches from the tip, e.g., from 2 to 5 inches from the tip.

Figure 7A:
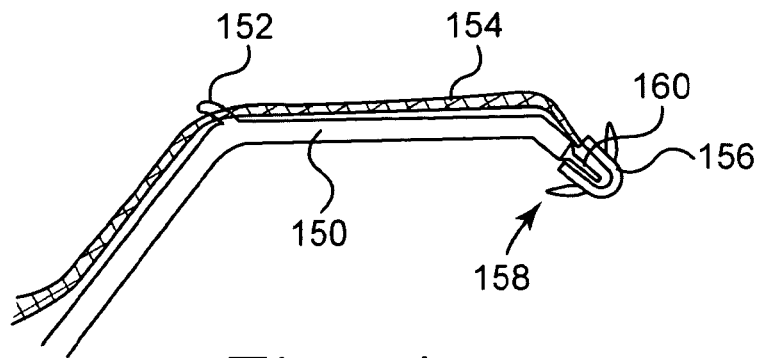
FIGS. 7A, 7B, and 7C illustrate embodiments of insertion tools and implants.

FIG. 7A illustrates an embodiment of an insertion tool that includes a pore engagement. Shaft 150 includes distal end 158 that includes cylindrical tip 160 that engages a smooth interior cylindrical bore of self-fixating tip 156 (shown in cross section) (non-cylindrical engagement surfaces can alternately be useful). Implant portion 154 extends from a proximal end of self-fixating tip 156, along an outer major bend (comprising cornered sections, alternately curved) of shaft 150. An aperture or pore of portion of implant 154 engages pore engagement 152, located on an outer major surface of the bend. Portion of implant 154 can be pulled taut to engage pore engagement 152, to pull self-fixating tip 156 snug against cylindrical tip 160. Shaft 150 can be used to place self-fixating tip at a location internal to a patient, such as by inserting self-fixating tip into soft tissue. During placement of self-fixating tip 156, tip 156 remains snug against cylindrical tip 160, to hold self-fixating tip at distal end 158. After placement of self-fixating tip, a distal end of portion of implant 154 can be pulled, which can slightly stretch portion of implant 154 and allow portion of implant 154 to become disengaged from pore engagement 152.

Figure 7B:
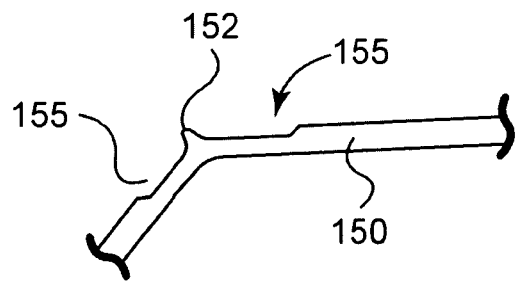
Figure 7C:
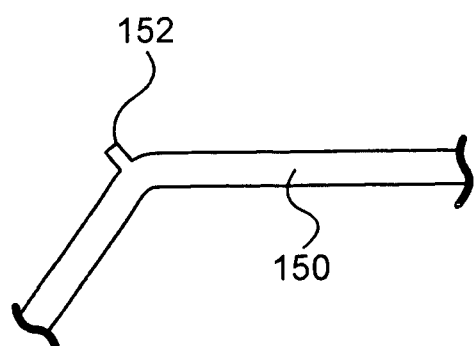

FIGS. 7B and 7C show alternate embodiments of pore extension 152, in the form of a rounded bump, or a straight extension, respectively. Rounded bump 152 of FIG. 7B was formed by removing (by machine) material from shaft 150, resulting in depressions 155.

In alternate embodiments (not illustrated) pore engagement 152 (of any of FIGS. 7A, 7B, and 7C) can be a moveable engagement that can moved and disengaged from portion of implant 154, by use of an actuator located at a proximal end of shaft 150.

Figure 8A:
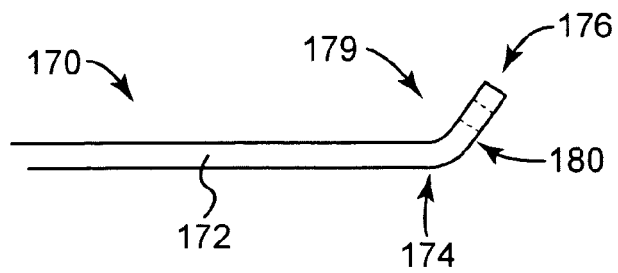
FIGS. 8A and 8B illustrate embodiments of adjusting tools.
Figure 8B:
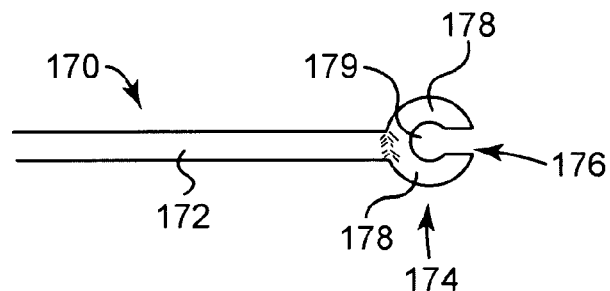

Another optional tool for use in methods of the invention, such as methods that include manipulation of an adjusting mechanism, is an adjusting tool. An adjusting tool can be an elongate tool that includes a distal end that engages an adjusting mechanism, to manipulate and optionally cause movement of the adjusting mechanism relative to a portion of implant. FIGS. 8A and 8B show side and top views of adjusting tool 170, useful for moving an adjusting engagement such as a grommet along a length of a segment of an implant such as a segment of an extension portion or a scaffold portion. Tool 170 includes elongate shaft 172 and distal end 174. Slot 176 at distal end 174 can be slid past a segment of implant to place a segment of implant at a location within aperture 179. Aperture 179 is defined in part by opposing arms 178 (illustrated to be curved, but optionally straight, angled, etc.) that extend laterally and optionally distally from a distal end of shaft 172, to define aperture 179 and slot 176. Bottom surfaces of arms 178 can be used to apply pressure to an adjusting engagement (e.g., grommet) located on the segment of implant, and move the grommet, preferably in a direction along the segment of implant to adjust a length of an extension portion or scaffold portion.

The dimensions of the slot and aperture can be useful to engage a segment of implant. A slot, for example, may define an opening that is in the range from 0.5 to 1.2 centimeters, e.g., from 0.5 to 1.0 centimeter. An aperture may have the same or similar dimensions, or may be the same width or wider than the slot, such as having a diameter in the range from 0.5 to 1.2, e.g., 0.5 to 1.0 centimeter. Surfaces for engaging an adjusting engagement may correspond to a size of surfaces of the adjusting engagement, such as having surfaces that match surfaces of a flange of a grommet.

Figure 9A:
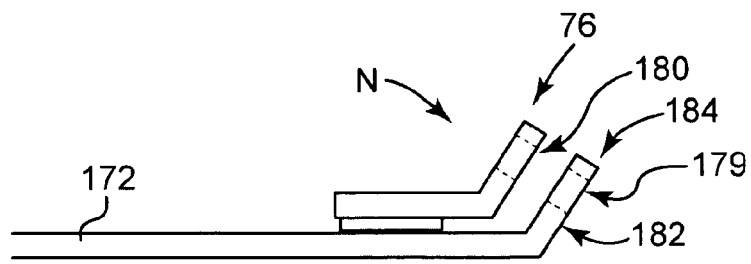
FIGS. 9A and 9B illustrate embodiments of adjusting tools.
Figure 9B:
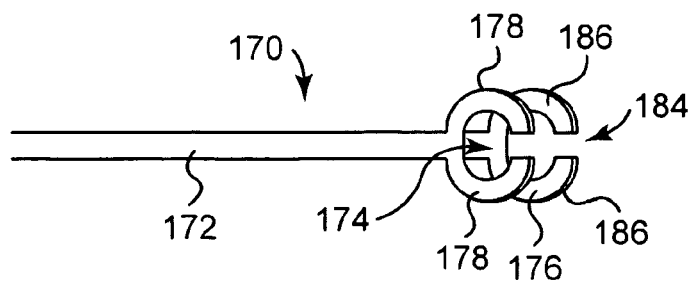

Another embodiment of adjusting tool is shown at FIGS. 9A and 9B. This embodiment of adjusting tool 170 includes features of tool 170 as illustrated at FIGS. 8A and 8B, and also includes an optional second set of arms around aperture 179, located in alignment with arms 178. FIGS. 9A and 9B show side and top views of this embodiment of adjusting tool 170. In addition to arms 178, defining features and surfaces as described, this embodiment of tool 170 includes a second set of arms, 184, that are aligned with arms 178 and that define additional length of aperture 179.

Still referring to FIGS. 9A and 9B, optional arms 186 are structured to prevent tissue from becoming lodged inside of an adjusting engagement (e.g. a grommet) during movement of grommet 32 in a direction N along a segment of implant. For instance, when an adjusting tool is used to move a grommet along a segment of mesh implant, within a patient, tissue may come into contact with the mesh or the grommet and (absent arms 186) can tend to be forced into the aperture of the grommet. Arms 186 become located on the side of the grommet that moves into tissue, and deflect and block tissue from entering an aperture of the grommet. Alternately, or additionally, second arms 186 can be used to move a two-way grommet in a direction opposite of the direction of movement provided by arms 178; i.e., this embodiment of an adjusting tool allows for a two-way grommet to be moved in two different directions (distally, and proximally) along an implant segment.

Figure 10A:
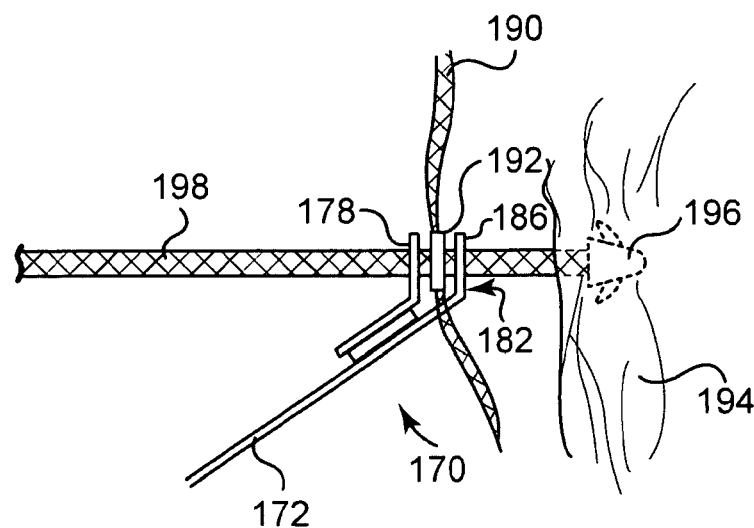
FIGS. 10A and 10B illustrate embodiments of adjusting tools, adjusting engagements, implants, and steps of related methods.
Figure 10B:
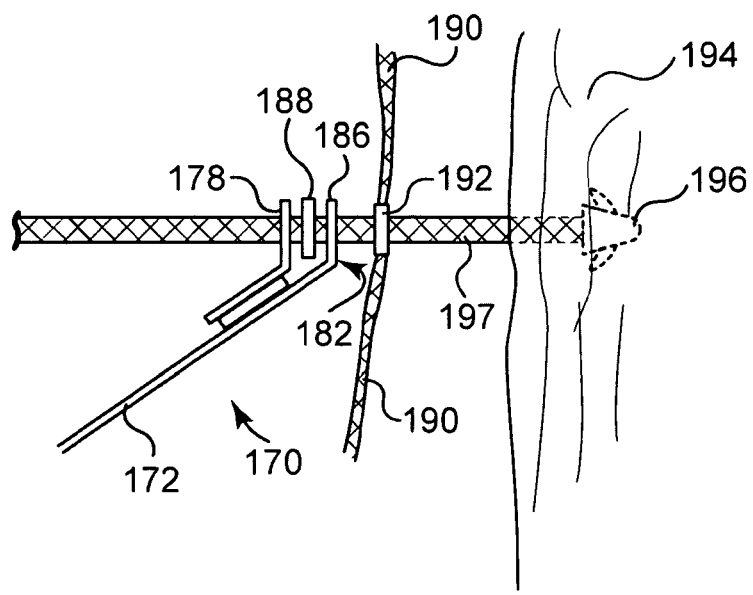

In use, slots 176 and 184 at distal end 174 can be slid over a segment of implant to place a segment of implant at a location within aperture 179 (defined by and between sets of arms 178 and 186). FIG. 10A shows that bottom surfaces 182 of arms 186 can deflect and block tissue from entering an aperture of adjusting engagement 192, which may be, e.g., a one-way or a two-way grommet used to adjust the location of implant portion 190 relative to implant segment 198, which includes tissue fastener 196 placed within tissue 194. FIG. 10B shows an alternate use of adjusting tool 170, by which a one-way adjusting engagement (grommet) 188 is manipulated to adjust toward a two-way grommet (192) attached to an implant portion (190), to secure a length of extension portion 197 between tissue 194 and two-way grommet 192.

In use, embodiments of implants as described can be implanted according to methods that include placement of a tissue support portion of an implant at a location to support pelvic tissue. One or more extension portions and optional scaffold portions are then placed for use in supporting the tissue support portion. For example, a tissue fastener at a distal end of an extension portion can be placed at internal tissue of the pelvic region such as muscle, ligament, tendon, fascia, bone, etc. Alternately, an extension portion may include a connector, for connecting to a tool that pulls the connector and extension portion through a tissue path leading to an external incision (e.g., at an external perirectal region, or through an obturator foramen and to an external incision at an inner thigh). As yet another alternative, an extension portion may not include a connector or a self-fixating tip but may be connected to tissue or led through a tissue path internal to the patient, or may be passed through a tissue path and an external incision. Optionally, a tissue fastener at a distal end of a scaffold portion can be connected to internal tissue of the pelvic region such as muscle, ligament, tendon, fascia, bone, etc. Alternately or additionally, an end of a scaffold portion can also be attached to a tissue support portion or an extension portion of an implant. An extension portion or a support portion piece can be attached to the scaffold portion at a location between the ends of the scaffold portion.

Embodiments of methods can be performed using a medial incision such as through a vaginal incision (for female anatomy) or perineal incision (for male anatomy), and by use of an insertion tool (e.g., any insertion tool described herein) that engages a distal end of the extension portion (such as by engaging a tissue fastener) and passes the distal end to a desired location within a pelvic region of a patient.

An end of an extension portion or scaffold portion can be attached to any desired tissue of the pelvic region, or passed through a desired tissue path to an external incision. To attach a distal end of an extension portion or scaffold portion to tissue, a tissue fastener can be attached at the end of the extension or scaffold portion. During installation of the implant, the tissue fastener can be attached to any desired tissue, for example soft tissue such as a muscle (e.g., of the obturator foramen, obturator internus, obturator externus, levator ani, coccygeous, iliococcygeous); ligament such as the sacrospinous ligament or surrounding tissue; tendon such as the arcus tendineus or surrounding tissue (e.g., a region of the arcus tendineus, see WO 2007/016083, published Feb. 8, 2007, and entitled "Methods and Symptoms for Treatment of Prolapse," the entirety of which is incorporated herein by reference); including tissue at or near an ischial spine, e.g., at a region of an ischial spine.

One specific example of a location for attaching an extension portion is at a tissue path that passes through or terminates at a region of an ischial spine. Tissue in a "region" of an ischial spine can be tissue that is within one centimeter from the ischial spine, including tissue of the levator ani muscle (e.g., iliococcygeous muscle) and arcus tendineus. A distal end of an extension portion or scaffold portion can be attached to tissue in this region, such as by a soft tissue fastener, optionally as described herein. The tissue in this region can be relatively thin compared to other tissue in the pelvic region, meaning that a tissue fastener may be adapted to securely attach to that thinner tissue. Examples of a tissue fasteners useful to attach to tissue of a region of the ischial include tissue fasteners illustrated and described herein, such as at FIGS. 3A, 3B, 4A, 4B, 4C, 5A, 5B, and 5C.

A method as described herein for treating vaginal prolapse, e.g., anterior or posterior vaginal prolapse (including vaginal vault prolapse), can include placing a tissue support portion at tissue of the anterior or posterior vagina or vaginal vault, and placing an extension portion extending from the tissue support portion to region of an ischial spine, preferably on both sides of a patient. Such a method can include additional optional steps that can be useful to improve support of vaginal tissue and, preferably, to restore an anatomically correct curve to vaginal tissue. Such a method can include an optional step of attaching an extension portion at a region of ischial spine, slightly anterior of the ischial spine at or near an arcus tendineus. Also optionally, additional length of the extension portion may be placed along and optionally attached to a length of arcus tendineus in an anterior direction from the ischial spine. Vaginal tissue may be placed in contact with the same extension portion that is placed in contact with or attached to the arcus tendineus, e.g., in a manner to provide Level 2 support of the medial vaginal tissue (e.g., sidewall tissue), also preferably to provide a vagina bend that is anatomically correct.

Figure 11A:
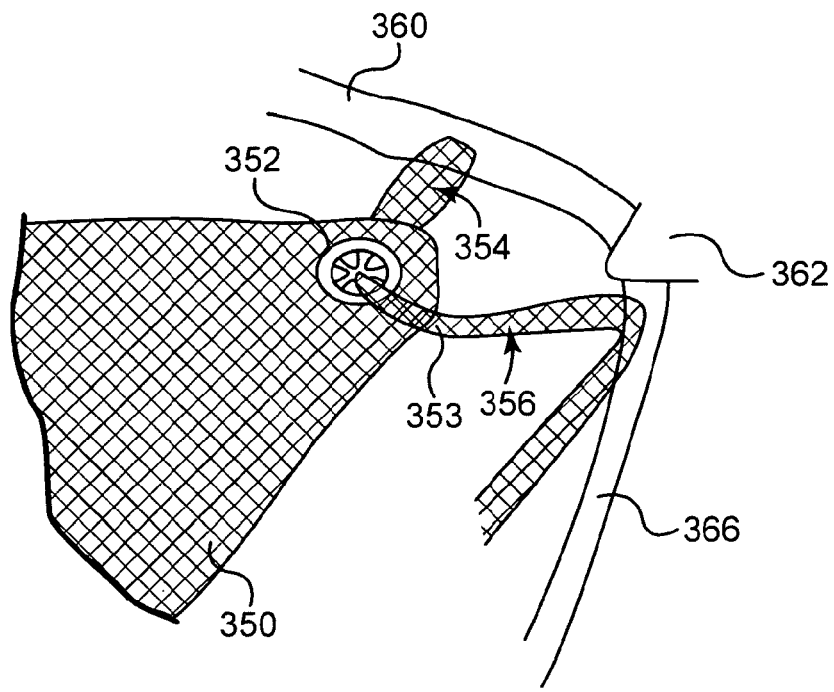
FIGS. 11A and 11B illustrate embodiments of implants and related anatomy for placement of the implants.
Figure 11B:
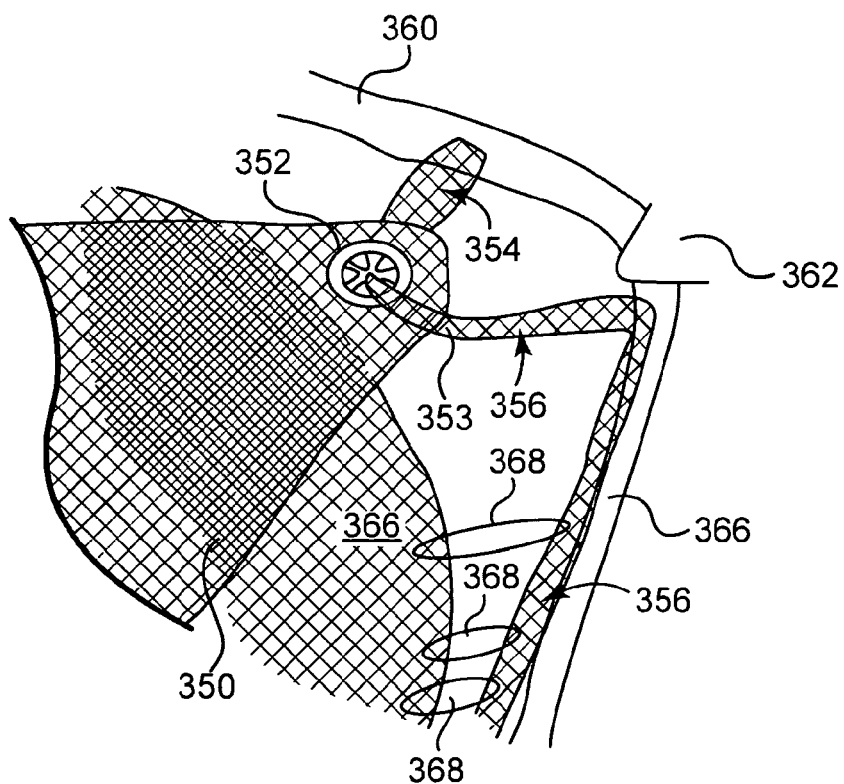

FIGS. 11A and 11B show anatomy and materials for achieving ischial spine support and optional Level 2 support for a posterior or an anterior vaginal implant, on a patient's left side. Support portion piece 350 of a vaginal implant, which may be a posterior or an anterior vaginal implant, is attached to vaginal tissue, preferably in a placement to put adjusting engagement (e.g., grommet) 352 at an apical location (near a vaginal apex). Extension portion piece 353 extends through adjusting engagement 352 in an adjustable fashion and defines posterior extension portion 354 between adjusting engagement 352 and sacrospinous ligament 360. Extension portion piece 353 also includes a "loose end" on the opposite side of adjusting engagement 352, which defines lateral extension portion 356 between adjusting engagement 352 and a location of a region of ischial spine, such as slightly anterior to ischial spine 362. A segment of lateral extension portion 356 that extends beyond the attachment at the region of ischial spine can be optionally placed along arcus tendineus 366, and optionally (and as illustrated at FIG. 11B) can be attached to a length of arcus tendineus 366 anterior to ischial spine 362. A tissue fastener (not shown), e.g., a self-fixating tip, is located at a distal end of posterior extension portion 354, and is secured to sacrospinous ligament 360.

In use, an implant is provided that includes a support portion piece (e.g., 350), that includes an adjustable extension portion piece (353) extending through an aperture (e.g., a one-way grommet) 352 located on the support portion piece, to define a posterior extension portion (354) of adjustable length and a lateral extension portion (356), the length of which increases as the length of posterior extension portion (354) is decreased. The distal end of posterior extension portion 354 is secured to sacrospinous ligament, and support portion piece 350 is secured to vaginal tissue to treat anterior prolapse, posterior prolapse, or vault prolapse. Preferably, aperture 352, from which posterior extension portion 354 and lateral extension portion 356 originate, can be located near a vaginal apex when support portion piece 350 is placed. The length of posterior extension portion 354 is adjusted by movement of extension portion piece 353 through aperture 352 (in other words moving aperture 352 in a direction toward distal end of posterior extension portions 354), and held frictionally by one-way grommet 352 to place support portion piece 350 as desired. Lateral extension portion 356 is extended to a location near and anterior to ischial spine 362, and attached to a region of ischial spine, such as at tissue of the arcus tendineus. Lateral extension portion 56 can be cut as desired.

In a variation on this method, lateral extension portion 356 can be cut at a length that will allow a segment of lateral extension portion 356 to be further extended laterally (and anteriorly) past ischial spine 362 at arcus tendineus 360, and along a length of arcus tendineus 362, optionally being attached to arcus tendineus 362 along that length. See FIG. 11B. As a further step, vaginal side wall tissue 366 can optionally be connected (e.g., by absorbable sutures, 368, or any other useful method) to lateral extension portion 356, which is extended along and optionally attached along a length of arcus tendineus 366, such as by use of absorbable sutures; this attachment step can also involve connecting (by the same sutures) to the arcus tendineus. Contacting and optionally connecting vaginal side wall tissue 366 to lateral extension portion 356 and arcus tendineus 366 can position the side wall tissue toward the arcus tendineus in a manner to provide Level 2 vaginal support by supporting side wall tissue 66, preferably to produce an anatomically correct vaginal bend.

Figure 12:
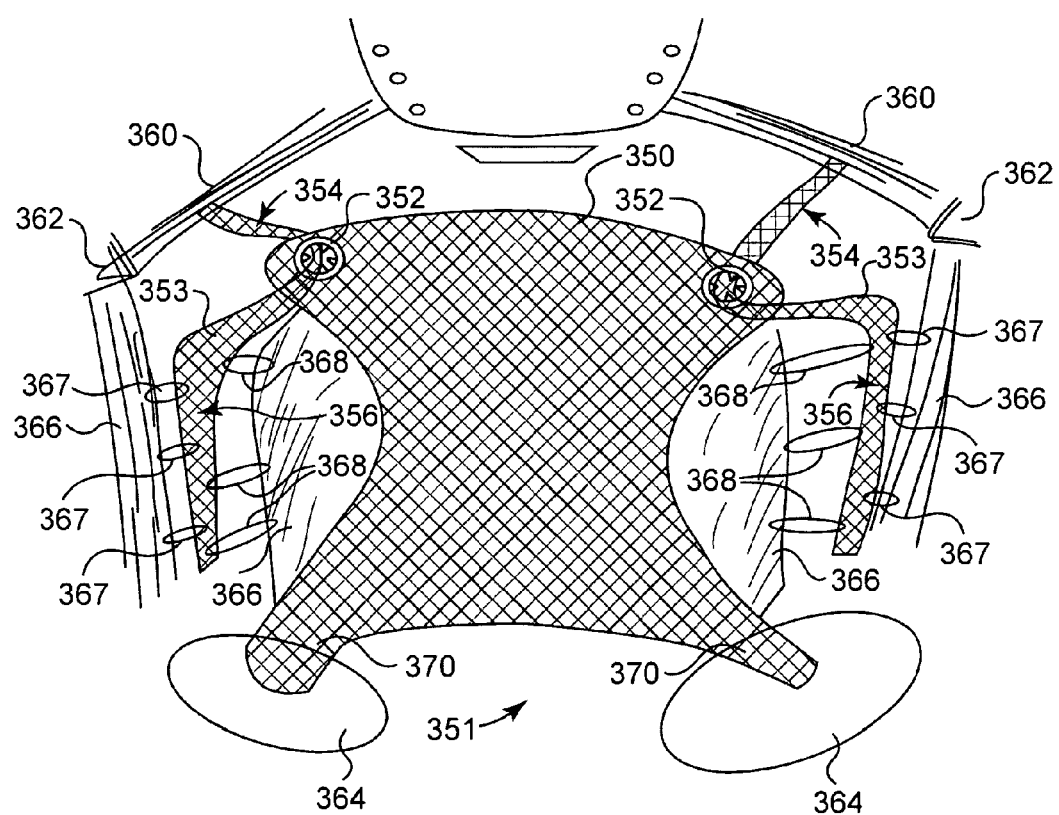
FIG. 12 illustrates embodiments of implants and related anatomy for placement of the implants.

A variation of this method is shown at FIG. 12, in an embodiment for treating anterior vaginal prolapse, with an additional step of attaching anterior extension portions of an implant at opposing obturator foramen. Anterior implant 351 includes adjustable extension portion pieces 353 (left and right sides) extending through aperture 352 located on tissue support portion piece 350. Each extension portion piece 353 defines a posterior extension portion 354 of adjustable length and a lateral extension portion 356, the length of which increases as the length of posterior extension portion (354) is decreased. The distal end of each posterior extension portion 354 is secured to sacrospinous ligament 360. Support portion piece 350 is secured to vaginal tissue to support an anterior prolapse. Preferably, aperture 352, from which posterior extension portion 354 and lateral extension portion 356 extend, can be located near a vaginal apex. The lengths of posterior extension portions 354 are adjusted as desired by movement of extension portion pieces 353 through apertures 352 (in other words moving aperture 352 in a direction toward distal end of posterior extension portions 354), and are held frictionally, to place support portion piece 350 as desired. Lateral extension portions 356 can be cut to a length to allow extension to locations near and anterior to ischial spine 362 and placement of additional length of lateral extension portions 356 along each opposing arcus tendineus 366. Each lateral extension portion 356 can be optionally attached to the length of arcus tendineus 366 using sutures 367 (or any other useful attachment). Useful lengths of lateral extension portion 356, measured from aperture 352 to a distal end, can be from about 3 to 5 centimeters, e.g., about 4 centimeters.

In the illustrated embodiment, opposing vaginal side wall tissues 366 are contacted with or optionally connected (e.g., by absorbable sutures, 368, or any other useful method) to opposing lateral extension portions 356 extending along opposing length of arcus tendineus 366.

Each of anterior extension portions 370, one on each side of support portion piece 350, is secured to opposing obturator foramen 364. A preferred method of attachment is by placing a tissue fastener such as a self-fixating tip (not shown), attached at ends of anterior extension portions 370, into tissue of each obturator foramen, preferably obturator internus muscle, preferably without penetrating the obturator membrane.

Regarding these methods that allow for Level 2 support by placement of an extension portion of implant along a length of arcus tendineus and in contact with vaginal sidewall tissue, after the implant is placed a physician would have the option of suturing the extension portion to the arcus tendineus to temporarily hold the extensions laterally. Alternately, a surgeon could merely allow an extension portion to lie laterally in contact with the arcus tendineus without placing sutures to attach the extension portion to the arcus tendineus. A mesh extension portion can tend to stick to tissue, and the amount of sticking could achieve the goal of temporarily setting a mesh extension portion in place near a vaginal sidewall.

In particular embodiments, after a vaginal incision is closed, the physician can suture the vaginal side wall, from inside the vagina, to the mesh extension portion located along the arcus tendineus, alternately or optional also suturing to the arcus tendineus. The mesh becomes located in-between the lateral vaginal wall and arcus tendineus. The mesh provides a scaffold between the vaginal wall and arcus tendineus, for tissue in-growth. Sutures may be placed using any technique or device, such as a curved pin end suture and any general medical instrument that allows manipulation of the suture, such as a hemostat. The optional suture can provide support and strength between the vaginal tissue (Level 2) and the arcus tendineus while tissue becomes in-grown into the mesh. After the suture biodegrades, the mesh has become fully in-grown and provides Level 2 support.

Advantageous features of methods as described and illustrated include that the methods can optionally and preferably be performed transvaginally using a single vaginal incision and no external incisions, to optionally provide multi-level support of vaginal tissue by placement of extension portions at one or more of the sacrospinous ligament, a region of an ischial spine, an arcus tendineus, and obturator foramen, with additional optional support of vaginal sidewalls by attachment to lateral extension portion 356 attached at opposing arcus tendineuses 366. Placement of a length of lateral extension portion 356 along arcus tendineus 366 can mitigate the possibility of a physician cutting the mesh arm too close to adjusting engagement 352. Also with this technique, extension portion piece 353 (adjustable relative to support portion piece 350) provides dual functions of adjusting lengths of extension portions (354 and 356), and when extended along an arcus tendineus allowing optional Level 2 tissue support and tissue ingrowth.

These and other exemplary methods described herein can allow for a combination of Level 1 and Level 2 support. Level 1 support (suspension of the apex of the vagina) may be provided by placement of an extension portion of an implant between a region of the vaginal apex to the sacrospinous ligament. Level 2 support (lateral attachment of vaginal sidewalls to pelvic side walls) may be provided by extending vaginal sidewalls—through an extension portion of an implant—to an arcus tendineus anterior to an ischial spine. Additionally, these methods can provide such support while avoiding the need for long-term external needle passes. Preferred method can restore a vaginal bend to an anatomically correct position. The methods can be applied to anterior and posterior products.

An implant used in these methods can be any useful implant that includes a tissue support portion suitable to support vaginal tissue, and extension portions that can extend to a sacrospinous ligament, a region of an ischial spine, and along a length of arcus tendineus.

Alternate methods and devices for providing a combination of Level 1 and Level 2 support for anterior prolapse can involve a tissue support portion having an anterior end and a posterior end; two opposing anterior extension portions can extend from the anterior end to be placed at opposing obturator foramen; two opposing lateral extension portions can extend laterally from sides between the anterior and posterior ends. A scaffold portion can extend from a location near the anterior end or at a mid-length position along the sides of the tissue support portion, such as by being connected (securely or adjustably) at an anterior extension portion, a lateral extension portion, or both. The scaffold portion extends from the anterior end or the mid-length location, along and distanced from sides of the implant, toward the posterior end, for connecting to a sacrospinous ligament. Additional extension portions may also make connections between the scaffold portion and sides of the tissue support portion, e.g., extending from locations at or near the posterior end of the tissue support portion to the scaffold portion.

Figure 13A:
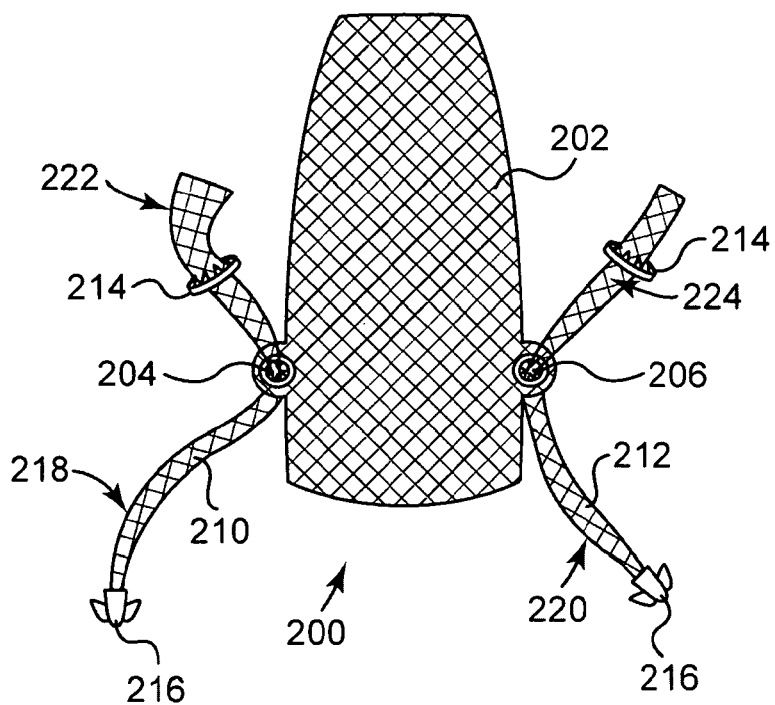
FIGS. 13A, 13B, and 13C illustrate embodiments of implants.
Figure 13B:
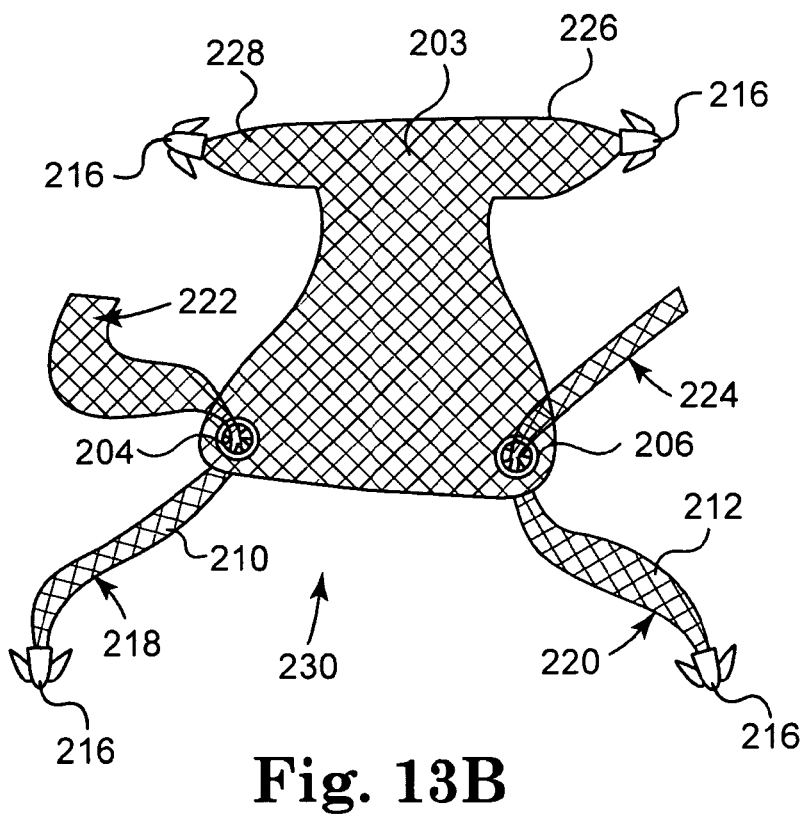
Figure 13C:
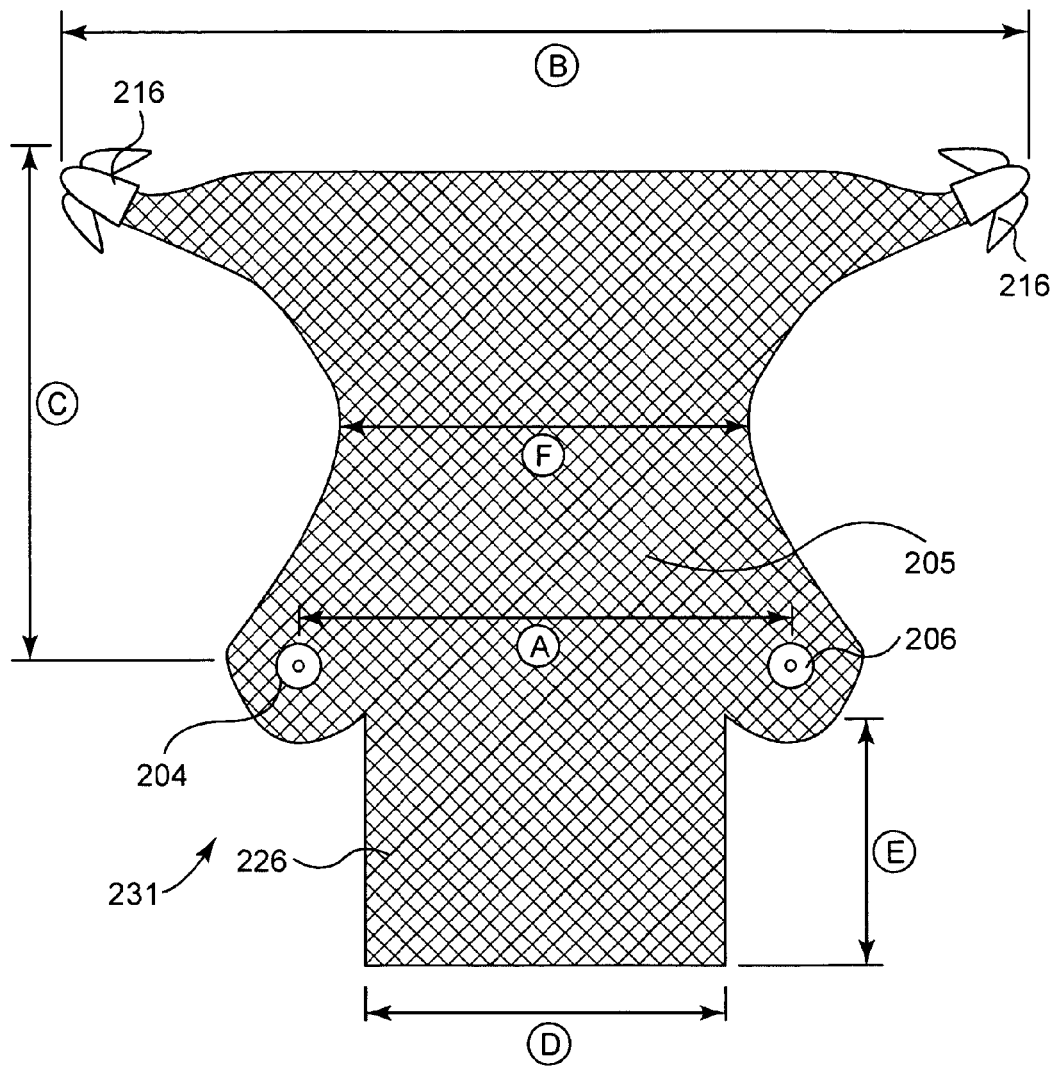

FIGS. 13A, 13B, and 13C illustrate exemplary multi-piece pelvic implants 200, 230, and 231. In these embodiments, an extension portion extends through an opening of a support portion piece that includes an adjusting engagement. The adjusting engagement can be a one-way adjusting engagement or a two-way adjusting engagement. If the adjusting engagement is a two-way adjusting engagement, a loose end of the extension portion piece can further include a second adjusting engagement that is a one-way adjusting engagement (see FIG. 13A) that can be moved in an direction toward the support portion piece and the two-way adjusting engagement to fix the length of an extension portion on the opposite side of the two-way adjusting engagement.

Referring to FIG. 13A, implant 200 can be used in methods as described, e.g., for treating posterior vaginal prolapse. Implant 200 includes support portion piece 202 having two-way apertures (e.g., grommets or openings) 204 and 206. Extension portion pieces 210 (left) and 212 (right) are threaded loosely through each of apertures 204 and 206, respectively, to allow substantially free two-way movement of each extension portion piece (210, 212) through each aperture (204, 206), for adjustment. The segment of left extension portion piece 210 that extends from one side of aperture 204, that includes self-fixating tip 216 at a distal end, is left posterior extension portion 218, and can be extended from aperture 204 to a (left) sacrospinous ligament to place self-fixating tip 216 at a (left) sacrospinous ligament. The segment of right extension portion piece 212 that extends from one side of aperture 206, that includes self-fixating tip 216 at a distal end, is right posterior extension portion 220, and can be extended from aperture 206 to a (right) sacrospinous ligament, to place self-fixating tip 216 at the (right) sacrospinous ligament. The segment of left extension portion piece 210 that extends from the other side of aperture 204, that includes two-way adjustment element 214 (the "loose" end), is left lateral extension portion 222, and can be extended from aperture 204 to a region of an ischial spine, and optionally along a length of arcus tendineus on a left side of a patient. The portion of right extension portion piece 212 that extends from the other side of aperture 206, that includes one-way adjustment element 14, is left lateral extension portion 224, and can be extended from aperture 206 to a region of an ischial spine and optionally along a length of arcus tendineus on a left side of a patient. Vaginal sidewall tissue can optionally be secured, e.g., by suture, to each of left lateral extension portion 224 and right lateral extension portion 222, attached to opposing arcus tendineuses, for Level 2 support.

Still referring to FIG. 13A, one-way adjusting engagements 214, located at each of left lateral extension portion 222 and right lateral extension portion 224, are optional. In use, an extension portion piece (210 or 212) can be adjusted as desired through an aperture (204, 206), e.g., to produce a desired length or tension on each posterior extension portion (218, 220). Support portion piece 202 and an extension portion piece (210, 212) can be placed internally as desired, and moved relative to each other by threading and sliding a support portion piece through either respective aperture on support portion piece 202. When desired positions are achieved, each adjusting engagement 214 can be slid to rest against an aperture (204, 206), to fix a maximum length of a posterior extension portions (218, 220), and also to adjust and fix lengths of corresponding lateral extension portions (222 and 224). Movement of a frictional adjustment element can be done by use of an adjustment tool as described herein. Extension portion pieces 210 and 212 are illustrated as being a length entirely of mesh, with no non-mesh portion. Alternately, extension portion pieces may be used that include a non-mesh portion, such as illustrated at FIGS. 6A and 6B, or otherwise described herein. A grommet management tool such as illustrated at FIG. 6C or as otherwise described herein can be used to place a grommet on each non-mesh portion of such extension portion pieces.

FIG. 13B illustrates another example of an implant (230), having components similar to those of implant 200, with the addition of two anterior extension portions (226 and 228) on an anterior end of support portion piece 203. This implant can be particularly useful for treating anterior prolapse. Support portion piece 203 of implant 230 can be placed to treat anterior vaginal prolapse. Adjusting engagements 204 and 206, in this illustrated embodiment, are shown as one-way adjusting engagements that allow extension portion pieces 210 and 212 to move in a direction to extend loose ends (lateral extension portions) 222 and 224, while shortening posterior extension portions 218 and 220; because these are one-way adjusting engagements, loose ends 222 and 224 do not include one-way adjusting engagements 214 as in implant 200 of FIG. 7A. Elements of implant 230 that are numbered similarly to features of implant 200, can function in the manner described for implant 20. Added elements of implant 230, right anterior extension portion 226 and left anterior extension portion 228, can be extended to locate self-fixating tips 216 (at their respective distal ends) at opposing right and left obturator foramen, respectively, of the patient.

FIG. 13C illustrates another example of an implant (231), having components similar to those of implant 230. Support portion piece 205 of implant 231 can be placed to treat anterior vaginal prolapse. The elements of implant 231 numbered similarly to features of implant 230 and can function in the manner described for implant 230. An additional element of implant 231, not present at implant 230, is posterior tissue support extension 226. Adjusting engagements 204 and 206 may be one-way adjusting engagements (e.g., grommets) or two-way adjusting engagements (e.g., grommets). Extension portion pieces (not shown) may include a length that is entirely mesh, or may include a mesh portion and a non-mesh portion, such as illustrated at FIGS. 6A and 6B or otherwise described herein. A grommet management tool as illustrated at FIG. 6C or as otherwise described herein can be used to place a grommet on each non-mesh portion of such extension portion pieces.

Exemplary dimensions of an implant as shown at FIG. 13C can be: length A, from 5 to 7 centimeters, e.g., from 5.5 to 6.5 centimeters; length B, from 10 to 12 centimeters, e.g., from 10.5 to 11.5 centimeters; length C, from 5.5 to 7.5 centimeters, e.g., from 6 to 7 centimeters; length D, from 3.5 to 5.5 centimeters, e.g., from 4 to 5 centimeters; length E, from 2 to 4 centimeters, e.g., from 2.5 to 3.5 centimeters; and length F, from 4 to 6 centimeters, e.g., from 4.5 to 5.5 centimeters.

Figure 14:
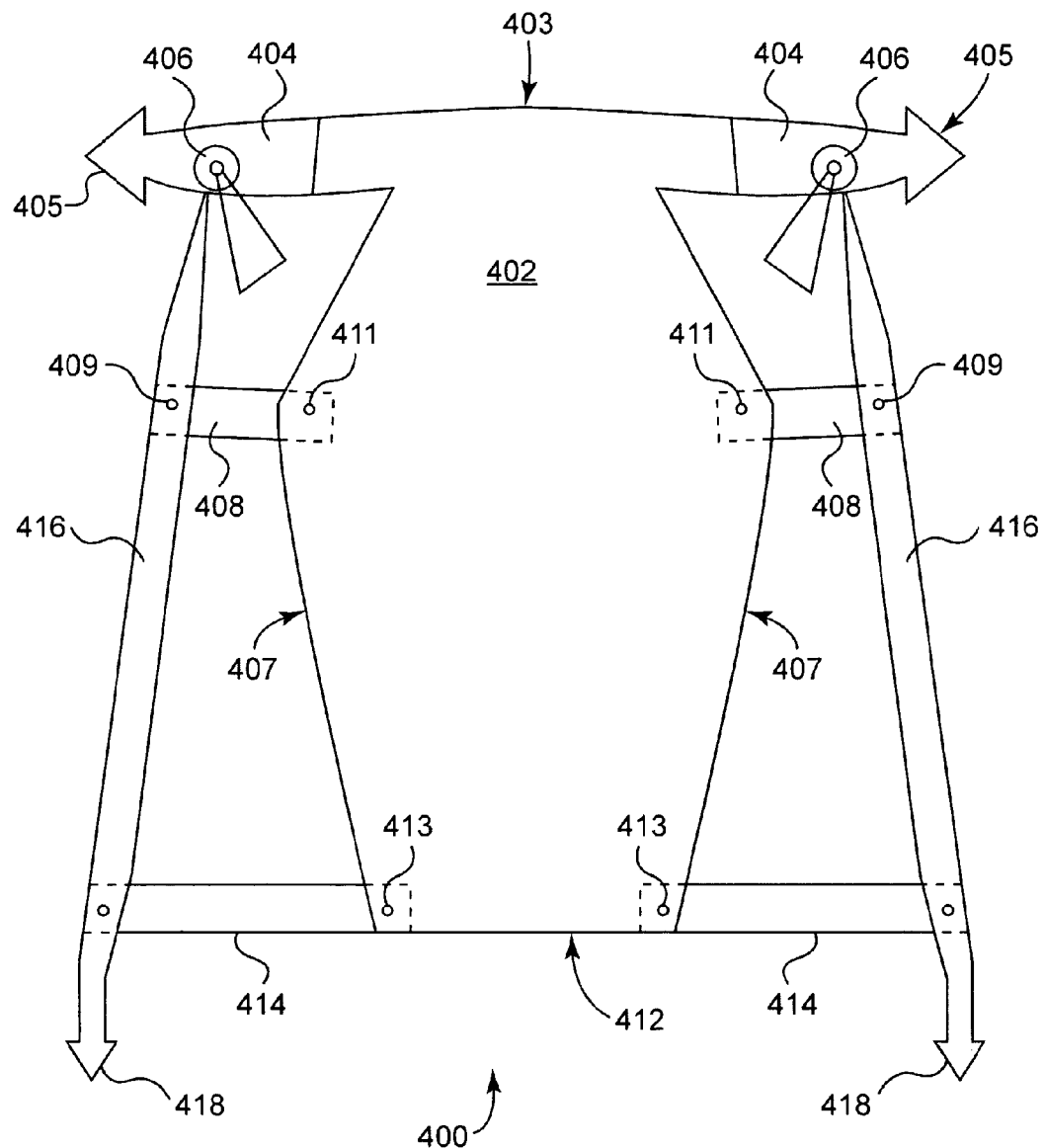
FIGS. 14 and 15 illustrate embodiments of implants.

Referring to FIG. 14, implant 400 can be useful to provide Level 1 and Level 2 support in treating anterior vaginal prolapse. Implant 400 includes tissue support portion 402, which may be synthetic (e.g., a mesh such as a large pore polypropylene ("LPP") mesh, or an extra large pore ("ELPP") mesh, or biologic (e.g., porcine, cadaveric, etc.). Anterior extension portions 404 extend from anterior end 403, to extension portion distal ends of that include tissue fasteners 405. An opposite end of tissue support portion 402, is posterior end 412. Extending between the ends are sides 407. Apertures 406, which may be adjusting engagements such as one-way or two-way grommets, are located at each anterior extension portion 404. Lateral extension portions 408 extend from each of sides 407 approximately mid-way (mid-length) between ends 403 and 412. Posterior extension portions 414 extend from each of sides 407, at posterior end 412. Scaffold portions 414 extend from apertures 406 (at anterior extension portions 404), along a length from end 403 to end 412 of tissue support portion 402, and are connected to ends of lateral extension portions 408 and posterior extension portions 414. Tissue fasteners (e.g., self-fixating tips) 418 are located at ends of scaffold portions 414, and can be secured to tissue of a sacrospinous ligament.

In use, implant 400 can be used to treat anterior vaginal prolapse with Level 1 and Level 2 support. Tissue support portion 402 is fastened to tissue of an anterior vagina, with anterior end 403 toward a patient's anterior to allow anterior extension portions 404 to extend to place tissue fixation devices 405 at opposing obturator foramen. Tissue support portion 102, e.g., near sides 107, is also attached to a mid-section of the vagina, optionally include sidewalls of the mid-section, and supported by extension portions to provide Level 2 support. Posterior end 412 can be secured to tissue near a vaginal apex to provide apical support. Tissue fasteners 418 are secured to sacrospinous ligaments on each of a left and a right side of the patient. Each of scaffold extension portions 416 can be adjusted as to length, to tension their engagement between the sacrospinous ligament and anterior extension portions 404, to which scaffold portions 416 are adjustably attached.

Dimensions of implant 400 can be as desired. To correspond generally to a width from one ischial spine to an opposing ischial spine, or from one arcus tendineus to an opposing arcus tendineus, within a pelvic region of a patient, which is about 9.5 centimeters, a width between two opposing distal ends of extension portions 408, such as from rivet 409 to rivet 409, can be, e.g., from 8 to 11 centimeters, or from about 8.5 to 10.5 centimeters. A width of a level 2 aspect of tissue support portion 402 can be sufficient to engage vaginal tissue sidewalls; e.g., a length between rivets 411 can be from about 5 to 7 centimeters, e.g., from 5.5 to 6.5 centimeters. A distance from end 302 (providing Level 3 support) and a mid-length location of the implant (e.g., rivet 411) can be, e.g., from abut 5 to 6 centimeters. A width of end 412, between rivets 413, can be, for example, from about 6 to 8 centimeters, e.g., from 6 to 7 centimeters.

Figure 15:
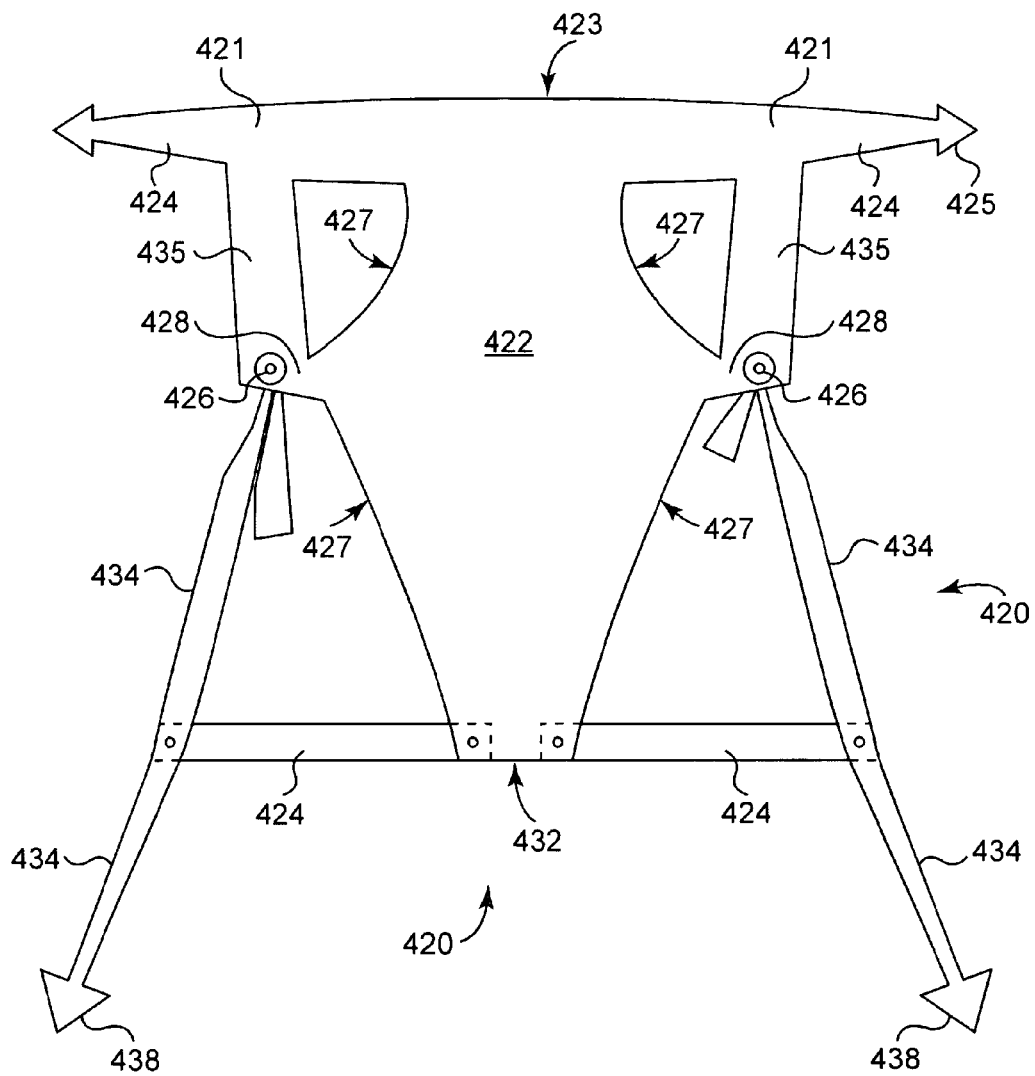

Referring to FIG. 15, implant 420 can be useful to provide Level 1 and Level 2 support in treating anterior vaginal prolapse. Implant 420 includes tissue support portion 422, which may be synthetic (e.g., a mesh, an LPP mesh, or an ELPP mesh) or biologic (e.g., porcine, cadaveric, etc.). Anterior extension portions 424 extend from anterior end 423 to distal ends that include tissue fixation elements 425. An opposite end of tissue support portion 422 is posterior end 432. Extending between the ends are sides 427. Apertures 426 are located at each lateral extension portion 428. Lateral extension portions 428 extend from each of sides 427 approximately mid-way (mid-length) between ends 423 and 432. Posterior extension portions 424 extend from each of sides 427 at posterior end 432. Scaffold portions 434 (which can optionally be considered to include segment 435) extend from apertures 426, along a length of tissue support portion 422, and are connected to ends of posterior extension portions 424. Tissue fasteners (e.g., self-fixating tips) 438 are located at ends of scaffold extension portions 434 and can be secured to tissue of a sacrospinous ligament.

At FIG. 15, the scaffold portions can be considered to be portions of the implant that extend from posterior tissue fasteners 438 to adjusting engagements 426 and further to anterior extension portions 424, connecting at secure engagements 421. By this convention segment 435 is considered to be a segment of each scaffold portion; the anterior end of the left-side scaffold portion is connected in a secure manner at location 421 to the anterior left-side extension portion, and the left-side scaffold portion includes an adjusting engagement (426) along the left-side scaffold portion length; and the anterior end of the right-side scaffold portion is connected in a secure manner at location 421 to the anterior right-side extension portion, and the right-side scaffold portion includes an adjusting engagement (426) along the right-side scaffold portion length. Each lateral extension portion 428 is optional and the adjusting engagements 426 may be considered to be (or may actually be) located near respective left and right sides (427) tissue support portion 422.

In use implant 420 can be used to treat anterior vaginal prolapse with Level 1 and Level 2 support. Tissue support portion 422 is fastened to tissue of an anterior vagina, with anterior end 423 toward a patient's anterior to allow anterior extension portions 424 to extend to place tissue fixation devices 425 at opposing obturator foramen. Tissue support portion 422, e.g., near sides 127, is also attached to sidewalls of vaginal tissue, to provide Level 2 support. Posterior end 432 can be secured to tissue near a vaginal apex to provide apical support. Tissue fasteners 438 are secured to sacrospinous ligaments on each of a left and a right side of the patient. Each of scaffold portions 434 can be adjusted as to length, to tension their engagement between the sacrospinous ligament and lateral extension portions 428.

Dimensions of implant 420 can be similar to those of implant 400.

Implants 200, 230, 231, 400, and 420 are primarily described in relation to treating vaginal prolapse, but these implants, and various of the separate features of these implants, (e.g., adjusting engagements, scaffold portions, and the general use and general and specific anatomic placement of these) may be used for treating other pelvic conditions. Also, any of these implants, or features of these implants, can be used in combination with any separate or combined components of implants and kits as described herein, such as the various tissue fasteners, adjusting tools, grommet management tools, insertion tools, adjusting engagements (e.g., grommets), etc., and for methods that include any of the variety of techniques, incisions, locations of internal attachment, and treated conditions.

Figure 16:
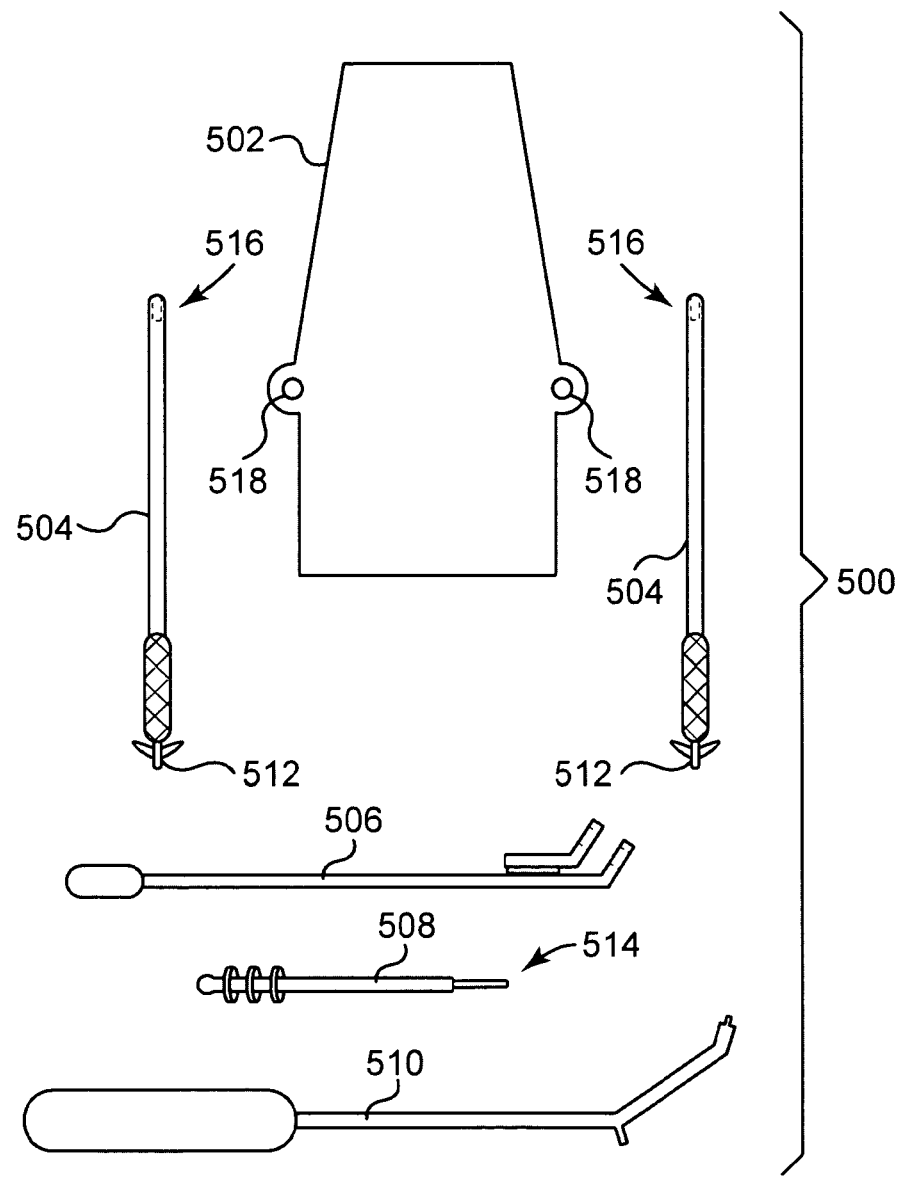
FIG. 16 illustrates embodiments of adjusting tools, adjusting engagements, implants, insertion tools, grommet management tools, and any embodiments of which can be assembled into a kit.

The implants and tools as described can be combined into kits that contain multiple different combinations of these tools. Any of the implants can be in a kit, with tools, extension portions pieces, support portion pieces, insertion tools, adjusting tools, grommet management tools, and tissue fasteners, in any combination. FIG. 16 illustrates such combinations. Kit 500 includes support portion piece 502 and two (optional) extension portion pieces 504. Extension portion pieces 502 include a mesh-portion and a non-mesh portion, but entirely mesh extension portion pieces could be used. Alternately, extension portion pieces can be absent and extension portions can be attached integrally to a tissue support portion. Optional adjusting tool 506 can be as described, e.g., as illustrated at FIGS. 8A and 8B, or 9A and 9B. Optional grommet management tool 508 can be as described, e.g., as illustrated at FIG. 6C or 6D. Optional insertion tool 510 can be as described, e.g., as illustrated at FIG. 7A, 7B, or 7C, or may be an alternate or previously-known insertion tool. Optional insertion tool 510 may engage tissue fasteners 512. End 514 of grommet management tool 508 can matingly engage ends 516 of non-mesh portions of extension portion pieces 504, such as at cylindrical bores (shown in shadow). Support portion piece 502 can be designed to support posterior vaginal tissue, anterior vaginal tissue, vaginal vault tissue, or another pelvic tissue, and can include optional features such as additional extension portions or scaffold portions or additional adjusting engagements (not shown). For example support portion piece 502 can comprise a support portion piece or implant as described or illustrated herein. Apertures 518 can be one-way adjusting engagements or two-way adjusting engagements.

Various embodiments disclosed herein can be combined with neuromuscular stimulation to treat pelvic prolapse and pain or discomfort associated with it or post-cancer or other reconstructive surgery.

The invention claimed is:

1. A kit comprising a pelvic implant comprising:
a support portion piece;
an extension portion piece; the extension portion piece comprising a mesh portion and a non-mesh portion, and the support portion piece comprising an adjusting engagement capable of adjustably engaging the extension portion piece;
a grommet management tool comprising a polymeric rod; and
grommets engaged with the grommet management tool along a length of the polymeric rod;
wherein the mesh portion comprises polymeric material and the non-mesh portion comprises a polymeric rod, and wherein a proximal end of the non-mesh portion matingly engages an end of the grommet management tool.

2. A kit according to claim 1 further comprising an adjusting tool.

3. A kit according to claim 1 comprising an insertion tool for placement of a tissue fastener of a pelvic implant, the insertion tool comprising a shaft having a pore engagement located along a length of the shaft.

4. A kit according to claim 1, further comprising an adjusting tool,
the adjusting tool comprising a shaft and a distal end, the distal end comprising a set of opposing arms extending laterally from the distal end of the shaft to comprise a slot.

5. A kit according to claim 4 wherein the adjusting engagement comprises a grommet, and arms of the adjusting tool engage a surface of the grommet, when the grommet is engaged with the extension portion piece.

6. A kit according to claim 5 wherein the grommet is selected from a one-way grommet and a two-way grommet.

7. A kit according to claim 4 comprising a first set of opposing arms extending laterally from the distal end of the shaft to comprise a slot, and a second set of opposing arms extending laterally from the distal end of shaft to comprise a slot.

8. A kit according to claim 4 wherein the pelvic implant has exactly two extension portions.

9. A kit according to claim 4 wherein the pelvic implant has exactly four extension portions.

10. A kit according to claim 1, wherein:
the adjusting engagement comprises an aperture, and
wherein a proximal end of the mesh portion connects to a distal end of the non-mesh portion,
a tissue fastener is attached to a distal end of the mesh portion, and
the non-mesh portion can pass through the aperture.

11. A kit according to claim 10 wherein the tissue fastener is a self-fixating tip.

12. A kit according to claim 10 wherein the adjusting engagement comprises a grommet.

13. A kit according to claim 1 wherein the non-mesh polymeric rod is integral to a proximal end of the mesh portion.

14. A kit according to claim 1 wherein a diameter of the grommet management tool matches a diameter of the non-mesh portion.

15. A kit according to claim 1 further comprising an adjusting tool that engages the grommet when the grommet is engaged with the extension portion piece.

16. A kit according to claim 1 wherein the pelvic implant has exactly two extension portions.

17. A kit according to claim 1 wherein the pelvic implant has exactly four extension portions.

18. (A method of placing a pelvic implant comprising
providing a kit according to claim 1, and
transferring a grommet from the grommet management tool to the non-mesh portion.

\* \* \* \* \*

UNITED STATES PATENT AND TRADEMARK OFFICE
CERTIFICATE OF CORRECTION

PATENT NO.         : 8,597,173 B2                                        Page 1 of 1
APPLICATION NO.    : 12/669099
DATED              : December 3, 2013
INVENTOR(S)        : O'Hern et al.

It is certified that error appears in the above-identified patent and that said Letters Patent is hereby corrected as shown below:

On the Title Page

On Page 3, in item (56), under "OTHER PUBLICATIONS", in Column 1, Lines 5-6, delete "G ynecologie Obstetrieue & Fertilite," and insert -- Gynecologie Obstetrique & Fertilite, --, therefor.

On Page 3, in item (56), under "OTHER PUBLICATIONS", in Column 1, Line 31, delete "Sugery," and insert -- Surgery, --, therefor.

On Page 3, in item (56), under "OTHER PUBLICATIONS", in Column 2, Line 38, delete "Sergical" and insert -- Surgical --, therefor.

On Page 3, in item (56), under "OTHER PUBLICATIONS", in Column 2, Line 40, delete "Prolift," and insert -- Profit, --, therefor.

In the Specification

In Column 4, Line 56, delete "fasteners; and" and insert -- fasteners, and --, therefor.

In Column 12, Line 29, delete "within slot." and insert -- within slot --, therefor.

In Column 15, Line 57, delete "two ends:" and insert -- two ends. --, therefor.

In Column 22, Line 23, delete "ingrowth." and insert -- in growth. --, therefor.

In Column 25, Line 34, delete "from abut" and insert -- from about --, therefor.

In the Claims

In Column 28, Line 36, in Claim 18, delete "(A method of placing a pelvic implant comprising" and insert -- A method of placing a pelvic implant comprising: --, therefor.

Signed and Sealed this
Twenty-sixth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,597,173 B2  Page 1 of 1
APPLICATION NO. : 12/669099
DATED : December 3, 2013
INVENTOR(S) : O'Hern et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 826 days.

Signed and Sealed this
Twenty-second Day of September, 2015

Michelle K. Lee
*Director of the United States Patent and Trademark Office*